US012226627B2

(12) United States Patent
Romero-Ortega et al.

(10) Patent No.: US 12,226,627 B2
(45) Date of Patent: Feb. 18, 2025

(54) DEVICES AND METHODS FOR NEUROMODULATION

(71) Applicant: Board of Regents, The University of Texas System, Austin, TX (US)

(72) Inventors: Mario I. Romero-Ortega, Coppell, TX (US); Stuart F. Cogan, Dallas, TX (US); Aswini Kanneganti, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 22 days.

(21) Appl. No.: 16/185,285

(22) Filed: Nov. 9, 2018

(65) Prior Publication Data

US 2019/0143102 A1    May 16, 2019

Related U.S. Application Data

(60) Provisional application No. 62/584,195, filed on Nov. 10, 2017, provisional application No. 62/584,203, filed on Nov. 10, 2017.

(51) Int. Cl.
*A61N 1/05*    (2006.01)
*A61N 1/36*    (2006.01)

(52) U.S. Cl.
CPC ........ *A61N 1/0556* (2013.01); *A61N 1/36007* (2013.01)

(58) Field of Classification Search
CPC ................... A61N 1/0556; A61N 1/36017
See application file for complete search history.

(56) References Cited

U.S. PATENT DOCUMENTS

| 3,157,181 A * | 11/1964 | Mccarty ............... A61N 1/0551 607/118 |
| 3,421,511 A * | 1/1969 | Wingrove ............ A61N 1/0556 607/118 |
| 3,654,933 A | 4/1972 | Hagfors |

(Continued)

FOREIGN PATENT DOCUMENTS

| FR | 3059476 A1 | 6/2018 |
| WO | 2006131912 A2 | 12/2006 |

(Continued)

OTHER PUBLICATIONS

Wel et al, "Iterative Electrodes Increase Neural Recruitment for Deep Brain Stimulation", IEEE, pp. 3419-3422, (2015).

(Continued)

*Primary Examiner* — William J Levicky
(74) *Attorney, Agent, or Firm* — Nutter, McClennen & Fish, LLP

(57) ABSTRACT

In one aspect, a neuromodulation device is described herein. In some embodiments, a neuromodulation device comprises a chamber operable to receive a nerve, at least one electrode disposed in the chamber, and a channel defined by two walls. In some embodiments, the channel of the device is in fluid communication with an interior of the chamber and an external surface of the device. In another aspect, methods of neuromodulation are described herein. In some embodiments, methods described herein can use one or more neuromodulation devices described herein.

19 Claims, 22 Drawing Sheets

(56) References Cited

U.S. PATENT DOCUMENTS

| | | | | |
|---|---|---|---|---|
| 4,487,210 | A * | 12/1984 | Knudsen | A61N 1/0541 607/137 |
| 5,038,781 | A | 8/1991 | Lynch | |
| 5,282,468 | A * | 2/1994 | Klepinski | A61N 1/0556 607/118 |
| 5,824,027 | A * | 10/1998 | Hoffer | A61N 1/0556 600/377 |
| 6,308,105 | B1 * | 10/2001 | Duysens | A61N 1/0551 607/118 |
| 8,652,187 | B2 | 2/2014 | Wells et al. | |
| 9,539,433 | B1 | 10/2017 | Wirbisky et al. | |
| 2002/0120309 | A1 | 8/2002 | Richmond et al. | |
| 2007/0129780 | A1 | 6/2007 | Whitehurst et al. | |
| 2012/0197336 | A1 | 8/2012 | Su | |
| 2012/0197356 | A1 * | 8/2012 | Wei | A61N 1/36171 607/74 |
| 2013/0090542 | A1 | 4/2013 | Kipke et al. | |
| 2017/0246453 | A1 * | 8/2017 | Fang | A61N 1/36171 |
| 2018/0093099 | A1 | 4/2018 | Cogan et al. | |
| 2018/0099139 | A1 | 4/2018 | Black et al. | |
| 2019/0060641 | A1 * | 2/2019 | Schüttler | A61N 1/0556 |
| 2019/0290902 | A1 | 9/2019 | Romero-Ortega et al. | |
| 2021/0290949 | A1 * | 9/2021 | Holinski | A61N 1/0556 |
| 2022/0062625 | A9 * | 3/2022 | Smith | A61N 1/0539 |
| 2024/0024668 | A1 * | 1/2024 | Coates | A61N 1/0558 |

FOREIGN PATENT DOCUMENTS

| | | |
|---|---|---|
| WO | 2013/150524 A1 | 10/2013 |
| WO | 2018/022838 A1 | 2/2018 |
| WO | 2020106986 A1 | 5/2020 |
| WO | 2020231440 A1 | 11/2020 |

OTHER PUBLICATIONS

Vitek, "Mechanisms of Deep Brain Stimulation: Exhibition or Inhibition", Movement Disorders, vol. 17, Suppl. 3, pp. S69-S72, Mar. 25, 2002.

Morris et al, "Effects of Electrode Configurtion and Stimulus Level on Rate and Level Discrimination with Cochlear Implants", JARO, pp. 211-223, Oct. 17, 2000.

Shah et al., "In vivo electrical stimulation of rabbit retina: Effect of stimulus duration and electrical field orientation", Experimental Eye Research, vol. 83, pp. 247-254, (2006).

Rattay et al., "Mechanisms of Electrical Stimulation with Neural Prostheses", Neuromodulation, vol. 6, No. 1, pp. 42-56, (2003).

Maynard et al., "The Utah Intracortical Electrode Array: a recording structure for potential brain-computer interfaces", Electroencephalography and clinical Neurophysiology, vol. 102, pp. 228-239, (1997).

Hu et al., "Scientiic profile of brain-computer interfaces: Bibliometric analysis in a 10-year period", Neuroscience Letters, vol. 635, pp. 61-66, Oct. 14, 2016.

Clements et al., "Regenerative Scaffold Electrodes for Peripheral Nerve Interfacing", IEEE Transactions on Neural Systems and Rehabilitation Engineering, vol. 21, No. 4, pp. 554-566, Jul. 2013.

Judy, "Neural Interfaces for Upper-Limb Prosthesis Control", IEEE Pulse, pp. 57-60, Mar. 22, 2012.

Thakor et al., "Bidirectional Peripheral Nerve Interface and Applications", IEEE, pp. 6327-6330, (2016).

Patel et al., "Insertion of linear 8.4 μm diameter 16 channel carbon fiber electrode for single unit recordings", J Neural Eng, vol. 12, No. 4, (2015) (38 pages).

Patel et al., "Chronic In Vivo Stability Assessment of Carbon Fiber Microelectrode Arrays", J Neural Eng, vol. 13, No. 6, Oct. 5, 2016.

Naples, et al., "A Spiral Nerve Cuff Electrode for Peripheral Nerve Stimulation", IEEE Transactions on Biomedical Engineering, vol. 35, No. 11, pp. 905-916, Nov. 1998.

Xue, et al., "Polymeric C-shaped cuff electrode for recording of peripheral nerve signal", Sensors and Actuators B: Chemical, pp. 640-648, (2015).

Kang et al., "Self-Closed Parylene Cuff Electrode for Peripheral Nerve Recording", Journal of Microelectromechanical Systems, vol. 24, No. 2, pp. 319-332, Apr. 2015.

Arreaga-Salas et al., "Integration of High-Charge-Injection-Capacity Electrodes onto Polymer Softening Neural Interfaces", ACS Applied Materials & Interfaces, vol. 7, pp. 26614-26623, Nov. 17, 2015.

Loeb et al., "Cuff electrodes for chronic stimulation and recording of peripheral nerve activty", Journal of Neuroscience Methods, vol. 64, pp. 95-103, (1996).

Sunderland et al., "Stress-Strain Phenomena in Human Peripheral Nerve Trunks", Brain, vol. 84, No. 1, pp. 102-119, 1961.

Raffe, "Principles of Peipheral Nerve Repair", Textbook of Small Animal Orthopaedics, Jan. 1, 1985 (26 pages).

Kwan et al., "Strain, stress and stretch of peripheral nerve Rabbit experiments in vitro and in vivo", Acta Orthopaedica Scandinavica, vol. 63, No. 3, pp. 267-272, (1992).

Rickett et al., "Functional and Mechanical Evaluation of Nerve Stretch Injury", J Med Syst, vol. 35, pp. 787-793, Apr. 6, 2010.

Cho et al., "Biocompatible SU-8-Based Microprobes for Recording Neural Spike Signals From Regenerated Peripheral Nerve Fibers", IEEE Sensors Journal, vol. 8, No. 11, pp. 1830-1836, Nov. 2008.

International Search Report issued in PCT/US2019/032691 mailed Jul. 18, 2019.

Written Opinion issued in PCT/US2019/032691 mailed Jul. 18, 2019.

Aboutalebi S.H., et al., "High-Performance Multifunctional Graphene Yarns: Toward Wearable All-Carbon Energy Storage Textiles," ACS Nano, vol. 8, Issue No. 3, pp. 2456-2466 (2014).

Barrese J.C., et al.,"Scanning electron microscopy of chronically implanted intracortical microelectrode arrays in non-human primates," J. Neural Eng., vol. 13, Issue No. 2, 44 pages (Apr. 2016).

Birmingham K., et al., "Bioelectronic medicines: a research roadmap," Nature Reviews, Drug Discovery, vol. 13, pp. 399-400 (Jun. 2014).

Boehler C., et al., "Nanostructured platinum grass enables superior impedance reduction for neural microelectrodes," Biomaterials, Department of Microsystems (IMTEK), University of Freiburg, vol. 67, pp. 346-353 (2015).

Boretius T., et al., "On the Stability of Poly-Ethylenedioxythiopene as Coating Material for Active Neural Implants," Artificial Organs, vol. 35, Issue No. 3, pp. 245-248 (2011).

Brummer S.B., et al., "Criteria for Selecting Electrodes for Electrical Stimulation: Theoretical and Practical Considerations," EIC Laboratories, Inc., 13 pages (1983).

Charkhkar H., et al., Chronic intracortical neural recordings using microelectrode arrays coated with PEDOT-TFB, Science Direct, 41 pages (2019).

Cheng C., et al., "A Water-Processable and Bioactive Multivalent Graphene Nanoink for Highly Flexible Bioelectronic Films and Nanofibers," Advanced Materials, pp. 1705452-1-1705452-11 (2017).

Cheng C., et al., "Functional Graphene Nanomaterials Based Architectures: Biointeractions, Fabrications, and Emerging Biological Applications," Chemical Reviews, vol. 117, pp. 1826-1914 (2017).

Christensen M.B., et al., "The foreign body response and morphometric changes associated with mesh-style peripheral nerve cuffs," Acta Biomaterialia, vol. 67, pp. 79-86 (2018).

Christie B.P., et al., "Long-term disability of stimulating spiral nerve cuff electrodes on human peripheral nerves," J. NeuroEngineering and Rehabilitation, vol. 17, Issue No. 70 (2017).

Cogan S.F., "Over-pulsing degrades activated iridium oxide films used for intracortical neural stimulation," J. Neuroscience Methods, vol. 137, pp. 141-150 (2004).

Cogan S.F., et al., "In Vitro Comparison of the Charge-Injection Limits of Activated Iridium Oxide (AIROF) and Platinum-Iridium Microelectrodes," IEEE Trans. Bio. Eng., vol. 52, Issue No. 9, pp. 1612-1614 (Sep. 2005).

Cogan S.F., et al., "Neural Stimulation and Recording Electrodes," Annu. Rev. Biomed. Eng., vol. 10, pp. 275-309 (2008).

Cogan S.F., et al., "Tissue damage thresholds during therapeutic electrical stimulation," J. Neural Eng., vol. 13, 13 pages (2016).

Cortes-Salazar F., et al., "Parylene C coated microelectrodes for scanning electrochemical microscopy," Electrochimica Acta, vol. 110, pp. 22-29 (2013).

(56) References Cited

OTHER PUBLICATIONS

Esrafilzadeh D., et al. "High-performance multifunctional graphene-PLGA fibers: toward biomimetic and conducting 3D scaffolds," University of Wollongong Australia, 38 pages (2016).
Fontes M.B.A., et al., "Electrodes for bio-application: recording and stimulation," 8th Ibero-American Congress on Sensors (Ibersensor 2012), Journal of Physics: Conference Series 421, 7 pages (2013).
Ganji M., et al., "Development and Translation of PEDOT:PSS Microelectrodes for Intraoperative Monitoring," Advanced Functional Materials, pp. 1700232-1-1700232-11 (2017).
Garrett D.J., et al., "Ultra-nanocrystalline diamond electrodes: optimization towards neural stimulation applications," J. Neural Eng., vol. 9, pp. 1-10 (2012).
Gerwig R., et al., "PEDOT-CNT composite microelectrodes for recording and electrostimulation applications: fabrication, morphology, and electrical properties," Frontiers in Neuroengineering, vol. 5, Article No. 8, pp. 1-11 (May 2012).
Green R.A., et al., "Conducting polymers for neural interfaces: Challenges in developing an effective long-term Implant," Biomaterials, vol. 29, pp. 3393-3399 (2008).
Green R.A., et al., "Impact of co-incorporating laminin peptide dopants and neurotrophic growth factors on conducting polymer properties," Acta Biomaterialia, vol. 6, pp. 63-71 (2010).
Green R.A., et al., "Substrate dependent stability of conducting polymer coating on medical electrodes," Biomaterials, vol. 33, pp. 5875-5866 (2012).
Guitchounts G., et al., "A carbon-fiber electrode array for long-term neural recording," J. Neural Eng., vol. 10, pp. 1-13 (2013).
Gunasekera B., et al., "Intracortical Recording Interfaces: Current Challenges to Chronic Recording Function," ACS Chemical Neuroscience, 16 pages (2015).
Harreither W., et al., "Carbon Nanotube Fiber Microelectrodes Show a Higher Resistance to Dopamine Fouling," Analytical Chemistry, vol. 85, pp. 7447-7453 (2013).
Harris A.R., et al., "Measuring the effective area and charge density of platinum electrodes for bionic devices," J. Neural Eng., vol. 15, pp. 046015-1-046015-13 (2018).
Hassler C., et al., "Characterization of parylene C as an encapsulation material for implanted neural prostheses," J. Bio. Mat. Res. B Appl. Biomat., vol. 93B, Issue No. 1, pp. 267-274 (2010).
Irwini Z.T., et al., "Chronic recording of hand prosthesis control signals via a regenerative peripheral nerve interface In a rhesus macaque," J. Neural Eng., vol. 13, pp. 046007-1-046007-11 (2016).
Jalili R., et al., "Formation and processability of liquid crystalline dispersions of graphene oxide," Mater. Horiz., vol. 1, pp. 87-91 (2014).
Jalili R., et al., "Scalable one-step wet-spinning of graphene fibers and yarns from liquid crystalline dispersions of graphene oxide: towards multifunctional textiles," Univ. of Wollongong Australia, 31 pages (2013).
Jiang K., et al., "Superaligned Carbon Nanotube Arrays, Films, and Yarns: A Road to Applications," Adv. Materi., vol. 23, pp. 1154-1161 (2011).
Keefer E.W., et al., "Carbon nanotube coating improves neuronal recordings," Nature, vol. 3, pp. 434-439 (2008).
Kim D., et al., "Conducting polymers on hydrogel-coated neural electrode provide sensitive neural recordings in auditory cortex," Acta Biomaterialia, vol. 6, pp. 57-62 (2010).
Kim Y., et al., "Electrochemical detection of dopamine in the presence of ascorbic acid using graphene modified electrodes," Biosensors and Bioelectronics, vol. 25, pp. 2366-2369 (2010).
Kim Y., et al., "Material considerations for peripheral nerve interfacing," MRS Bulletin, vol. 37, pp. 573-580 (Jun. 2012).
Kou L., et al., "A Mini Review on Nanocarbon-Based 1D Macroscopic Fibers: Assembly Strategies and Mechanical Properties," Nano-Micro. Lett., vol. 9, Issue No. 51, 18 pages (2017).
Kozai T.D., et al., "Chronic In Vivo Evaluation of PEDOT/CNT for Stable Neural Recordings," IEEE Trans. Bio. Eng., vol. 63, Issue No. 1, pp. 111-119 (Jan. 2016).
Kozai T.D.Y., et al., "Chronic tissue response to carboxymethyl cellulose based dissolvable insertion needle for ultra-small neural probes," Biomaterials, pp. 1-14 (2014).
Kozai T.D.Y., et al., "Ultrasmall implantable composite microelectrodes with bioactive surfaces for chronic neural interfaces," Nature Materials, vol. 11, pp. 1065-1073 (Nov. 2012).
Lacour S.P., et al., "Flexible and stretchable micro-electrodes for in vitro and in vivo neural interfaces, " Med. Biol. Comput., vol. 48, pp. 945-954 (2010).
Lee Y., et al., "Strategies for Minimizing Glial Response to Chronically-implanted Microelectrode Arrays for Neural Interface," Biomed. Eng. Lett., vol. 4, pp. 120-128 (2014).
Li D., et al., "Processable aqueous dispersions of graphene nanosheets," Nature Nantechnology, vol. 3, pp. 181-185 (Feb. 2008).
Lissandrello, C.A., et al., "A Micro-scale printable nanoclip for electrical stimulation and recording in small nerves". J. Neural Eng., vol. 14, published Mar. 21, 2017 (12 pages).
Liu T., et al., "Implantable Graphene-based Neural Electrode Interfaces for Electrophysiology and Neurochemistry in In Vivo Hyperacute Stroke Model," Applied Materials and Interfaces, pp. 187-196 with supporting information (2015).
Lu Y., et al., "Electrodeposited polypyrrole/carbon nanotubes composite films electrodes for neural interfaces," Biomaterials, vol. 31, pp. 5169-5181 (2010).
Lu Y., et al., "Flexible Neural Electrode Array Based-on Porous Graphene for Cortical Microstimulation and Sensing," Scientific Reports, 9 pages (Sep. 2016).
Luo X., et al., "Highly stable carbon nanotube doped poly(3,4-ethylenedioxythiophene) for chronic neural stimulation," Biomaterials, vol. 32, pp. 5551-5557 (2011).
Mccallum G.A., et al., "Chronic interfacing with the autonomic nervous system using carbon nanotube (CNT) yarn electrodes," Scientific Reports, vol. 7, pp. 11723-1-11723-14 (Sep. 2017).
Mcdonald D.M., et al., Morphology of the rat carotid sinus nerve., J. Neurocytology, vol. 12, pp. 373-392 (1983).
Naples G.G., et al., "A Spinal Nerve Cuff Electrode for Peripheral Nerve Stimulation," IEEE Trans. Bio. Eng., vol. 35, Issue No. 11, pp. 905-916 (Nov. 1988).
Navarro X., et al., "A critical review of interfaces with the peripheral nervous system for the control of neuroprostheses and hybrid bionic systems," J. Peripheral Nerv. Sys., vol. 10, pp. 229-258 (2005).
Negi S., et al., "Neural Electrode Degradation from Continuous Electrical Stimulation: Comparison of Sputtered and Activated Iridium Oxide," J. Neurosci. Meth., vol. 186, Issue No. 1 (Jan. 2010).
Ordonez J.S., et al., "Cuff Electrodes for Very Small Diameter Nerves—Prototyping and First Recordings In Vivo," IEEE, pp. 6846-6849 (2014).
Otchy, T.M., et al., "Printable microscale interfaces for long-term peripheral nerve mapping and precision control", Nature Communications 11, 4191 (2020), retrieved from the internet at //https://doi.org/10.1038/s41467-020-18032-4//, 16 pages.
Park S., et al., "Nanopourous Pt Microelectrode for Neural Stimulation and Recording: In Vitro Characterization," J. Phys. Chem. C., vol. 114, pp. 8721-8726 (2010).
Potter K.A., et al., "Stab injury and device implantation within the brain results in inversely multiplastic neuroinflammatory and neurodegenerative responses," J. Neural Eng., vol. 9, 14 pages (2012).
Poulin P., et al., "Superflexibility of graphene oxide," Proceedings of the National Academy of Sciences of the U.S.A., vol. 113, Issue No. 40, pp. 11088-11093 (Oct. 2016).
Qi D., et al., "Design of Architectures and Materials in In-Plane Micro-supercapacitors: Current Status and Future Challenges," Adv. Mater., vol. 29, pp. 1602802-1-1602802-19 (2017).
Restaino S.M., et al., "Biomechanical and functional variation in rat sciatic nerve following cuff electrode Implantation," J. Neuro. Rehab., vol. 11, Issue No. 73, 10 pages (2014).
Rho H., et al., "Metal nanfibrils embedded in long free-standing carbon nanotube fibers iwth a high critical current display," NPG Asia Materials, vol. 10, pp. 146-155 (2018).

(56) References Cited

OTHER PUBLICATIONS

Rivnay J., et al., "Next-generation probes, particles, and proteins for neural interfacing," Science Advances, vol. 3, pp. e1601649-1-e1601649-20 (Jun. 2017).
Rutten W.L.C., et al., "Selective Electrical Interfaces with the Nervous System," Annu. Rev. Biomed. Eng., vol. 4, pp. 407-452 (2002).
Sahni D., et al., Biocompatibility of pristine graphene for neuronal interface, J. Neurosurg. Pediatrics, vol. 11, pp. 675-583 (2013).
Schrimer K.S.U., et al., "Conductive Composite Fibres from Reduced Graphene Oxide and Polypyrrole Nanoparticles," J. Mat. Chem. B., 10 pages (2013).
Sevcencu C., et al., "A neural blood pressure marker for bioelectronic medicines for treatment of hypertension," Biosensors and Bioelectronics, vol. 98, 6 pages (2017).
Stein R.B., et al., "Principles Underlying New Methods for Chronic Neural Recording," Le J. Canadien Des Sci. Neuro., pp. 235-244 (Aug. 1975).
Tan D.W., et al., "Stability and selectivity of a chronic, multi-contact cuff electrode for sensory stimulation in human amputees," J. Neural Eng., vol. 12, 10 pages (2015).
Tjoa V., et al., "Facile Photochemical Synthesis of Graphene-Pt Nanoparticle Composite for Counter Electrode in Dye Sensitized Solar Cell," ACS Appl. Mater. Interfaces, pp. 3447-3452 (2012).
Tong W., et al., "Optimizing growth and post treatment of diamond for high capacitance neural interfaces," Biomaterials, vol. 104, pp. 32-42 (2010).
Tybrandt K., et al., "High-Density Stretchable Electrode Grids for Chronic Neural Recording," Adv. Mater., vol. 30, pp. 1706520-1-1706520-7 (2018).
Venkatraman S., et al., "In Vitro and In Vivo Evaluation of PEDOT Microelectrodes for Neural Stimulation and Recording," IEEE Trans. Neural Sys. Rehab. Eng., vol. 19, Issue No. 3 (Jun. 2011).
Vince V., et al., "Anti-TNF-a reduces the inflammatory reaction associated with cuff electrode implantation around the sciatic nerve," J. Neuro., vol. 165, pp. 121-128 (2005).
Vitale F., et al., "Fluidic Microactuation of Flexible Electrodes for Neural Recording," Nano Letters, 10 pages (Dec. 2017).
Vitale F., et al., "Neural Stimulation and Recording with Bidirectional, Soft Carbon Nanotube Fiber Microelectrodes," ACS Nano, vol. 9, Issue No. 4, pp. 4465-1174 (2015).
Wang J., et al., "Carbon Nanotube Fiber Microelectrodes," J. Am. Chm. Soc., vol. 125, pp. 14706-14707 (2003).
Wang K., et al., "High-Performance Graphene-Fiber-Based Neural Recording Microelectrodes," Adv. Mater., vol. 31, pp. 1805867-1-1805867-10 (2019).
Wang K., et al., "Neural Stimulation with a Carbon Nanotube Microelectrode Array," Nano Lett., vol. 6, Issue No. 9, pp. 2043-2048 (2006).
Wang M., et al., "Nanotechnology and Nanomaterials for Improving Neural Interfaces," Adv. Funct. Mater., pp. 1700905-1-1700905-28 (2017).
Weiland J.D., et al., "In Vitro Electrical Properties for Iridium Oxide Versus Titanium Nitride Stimulating Electrodes," EEE Trans. Bio. Eng., vol. 49, Issue No. 12, pp. 1574-1579 (Dec. 2002).
Weremfo A., et al., "Investigating the Interfacial Properties of Electrochemically Roughened Platinum Electrodes for Neural Stimulation," Langmuir, vol. 31, pp. 2593-2599 (2015).
Wilks S.J., et al., "Poly(3,4-ethylenedioxythiophene) as a microneural interface material for electrostimulation," Frontiers in Neuroengineering, vol. 2, Article 7, pp. 1-8 (Jun. 2009).
Wodlinger B., "Recovery of neural activity from nerve cuff electrodes," 33rd Annual International Conf. of the IEEE EMBS, Boston, Massachusetts, 4 pages (Aug.-Sep. 2011).
Won S.M., et al., "Recent Advances in Materials, Devices, and Systems for Neural Interfaces," Adv. Mater., vol. 30, pp. 1800534-1-1800534-19 (2018).
Yoon I., et al., "Intracellular Neural Recording with Pure Carbon Nanotube Probes," PLoS One, vol. 8, Issue No. 6, pp. e65715-1-e65715-6 (Jun. 2013).
Zhang H., et al., Tissue-Compliant Neural Implants from Microfabricated Carbon Nanotube Multilayer Composite, ACS Nano, vol. 7, Issue No. 9, pp. 7619-7629 (2013).
Zhao S., et al., "Programmable Hydrogel Ionic Circuits for Biologically Matched Electronic Interfaces," Adv. Mater., vol. 30, pp. 1800598-1 -1800598-10 (2018).
Zheng X., et al., "Hierarchically porous sheath-core graphene-based fiber-shaped supercapacitors with high energy density," J. Mater. Chem. A., vol. 6, pp. 896-907 (2018).
Zhou W., et al., "Single wall carbon nanotube fibers extruded from super-acid suspensions: Preferred orientation, electrical, and thermal transport," J. Appl. Phy., vol. 95, Issue No. 2, pp. 649-655 (Jan. 2004).
Extended European Search Report for Application No. 19928380.5, dated Nov. 29, 2022, 7 pages.

\* cited by examiner

BP = Bond Pad
E = Electrode stimulating electrode record EMG

DEVICES AND METHODS FOR NEUROMODULATION

CROSS REFERENCE TO RELATED APPLICATIONS

This application claims priority pursuant to 35 U.S.C 119(e) to U.S. Provisional Patent Application No. 62/584,195, filed on Nov. 10, 2017, and U.S. Provisional Patent Application No. 62/584,203, filed on Nov. 10, 2017, each of which is hereby incorporated by reference in its entirety.

FIELD

This disclosure is related to devices and methods for neuromodulation, and specifically, methods of preventing and/or treating perineal dysfunction.

BACKGROUND

Silicone nerve cuff electrodes are used extensively in a broad range of clinical applications including stimulation of the vagus nerve for the treatment of epilepsy, depression and tinnitus, sacral or pudendal nerves for lower urinary tract disorders, and tibial nerve for rehabilitation of patients with drop foot.

Nerve targets for these applications consist of somatic and autonomic nerves, of which somatic nerves are large, robust and easy to interface. However, therapeutic neural stimulation for targeted regulation of visceral organ function requires miniature implantable electrode devices which interface with autonomic nerves with minimal to no effect on the inherent nerve anatomy. Autonomic nerves have small diameter, usually less than 200 µm and are very fragile, making them difficult to handle and increasing the risk of damage when implanting a traditional cuff electrode.

Conventional electrode implantation and securing methods involve suturing and/or use of medical grade epoxy. Securing cuff electrodes to small and fragile nerve often causes damage due to excessive manipulation. This is exacerbated in nerves that are located near to blood vessels or adjacent to internal organ targets. Thus, there is a need a need for improved neuromodulation devices that minimize nerve manipulation and properly anchor electrodes to small nerves and nerve fibers.

Dysfunctional perineal muscles can manifest as various impediments to normal bodily functions, including, but not limited to micturition, erection, and orgasm. Currently, Urinary incontinence affects more than 200 million people worldwide, and pelvic floor dystonia is often seen in the clinical setting of overactive bladder.

Pelvic floor muscle training (PFMT) has become a widely accepted first choice of treatment for stress urinary incontinence. PFMT can generate improvement rates of 50-70%. Despite the improvements, inaccurate performance and low patient compliance (dropout rate of 39%) drastically limits this approach.

Transvaginal electrical stimulation and pelvic floor muscle training are commonly used for both female stress urinary incontinence and overactive bladder symptoms and appear to be effective at various levels of electrical stimulation. The mechanism of neuromodulation has been postulated to mediate the reflex inhibition of detrusor contraction by the activation of afferent fibers within the pudendal nerve. However, intravaginal and anal plug electrodes are intolerable for some patients due to pain, discomfort or mucosal injury. Moreover, selective stimulation of targeted muscles and nerves is not possible using current technologies and non-selective neuromodulation can lead to unwanted side effects. Thus, improved methods of neuromodulating perineal muscles are needed.

SUMMARY

In one aspect, a neuromodulation device is described herein, which in some embodiments, provides one or more advantages over current neuromodulation devices. For example, a device described herein, in some cases, can comprise a unique L-shaped longitudinal channel that allows access to the recording/stimulating chamber. This design offers a slide-in-lock mechanism using a slit opening calculated to be 10-50% of the nerve diameter, through which a nerve can be inserted via a soft and brief stretching of the nerve tissue, and then released or relaxed or "unstretched" inside an electrode chamber. The design facilitates facile and rapid implantation of the neuromodulation device while minimizing nerve manipulation to prevent nerve damage during implantation.

In some embodiments, a neuromodulation device described herein comprises (i) a chamber operable to receive a nerve, (ii) at least one electrode disposed in the chamber, and (iii) a channel defined by two walls. In some embodiments, the channel is in fluid communication with an interior of the chamber and an external surface of the device. In some instances, the channel comprises an average width that is 10-50% smaller than an average diameter of the chamber. In some instances, the channel is non-linear.

In another aspect methods of treating and/or preventing perineal dysfunction are disclosed herein. Methods disclosed herein can provide one or more advantages over current methods of preventing and/or treating perineal dysfunction. For example, methods described herein can be more effective in neuromodulating specific individual pelvic floor muscles, unlike current methods, which are non-specific and can lead to unwanted side effects caused by stimulation of sacral roots or the pudendal nerve. In some embodiments a method comprises neuromodulating one or more pelvic floor muscles. For example, a step of neuromodulating can be achieved using any device described herein.

These and other embodiments are described in greater detail in the following detailed description.

BRIEF DESCRIPTION OF THE DRAWINGS

FIG. 1A illustrates design and fabrication of the neuroclip electrode according to one embodiment described herein. Figure may not be to scale.

FIG. 2 illustrates the "slide-in-lock" mechanism of the neuroclip according to one embodiment described herein.

FIG. 3B illustrates a SU-8 neuroclip device with gold electrode and wired to an external omnetics connector, according to one embodiment described herein.

DETAILED DESCRIPTION

Figure 1A:
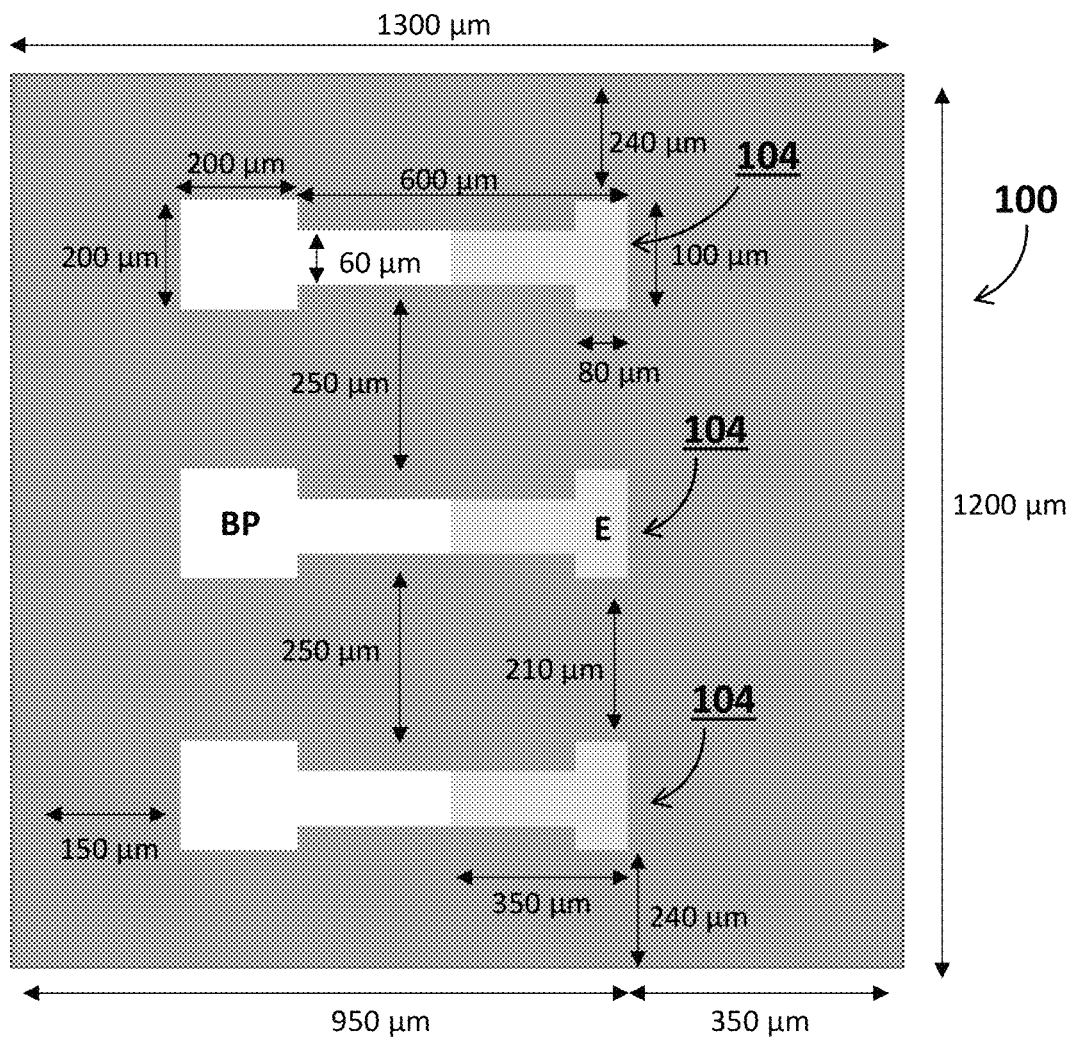
FIG. 1A is a top view of a schematic representation of a neuromodulation device described herein.
Figure 1A:
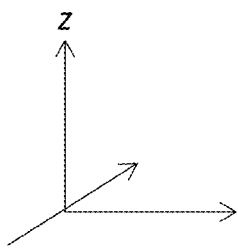
Figure 1B:
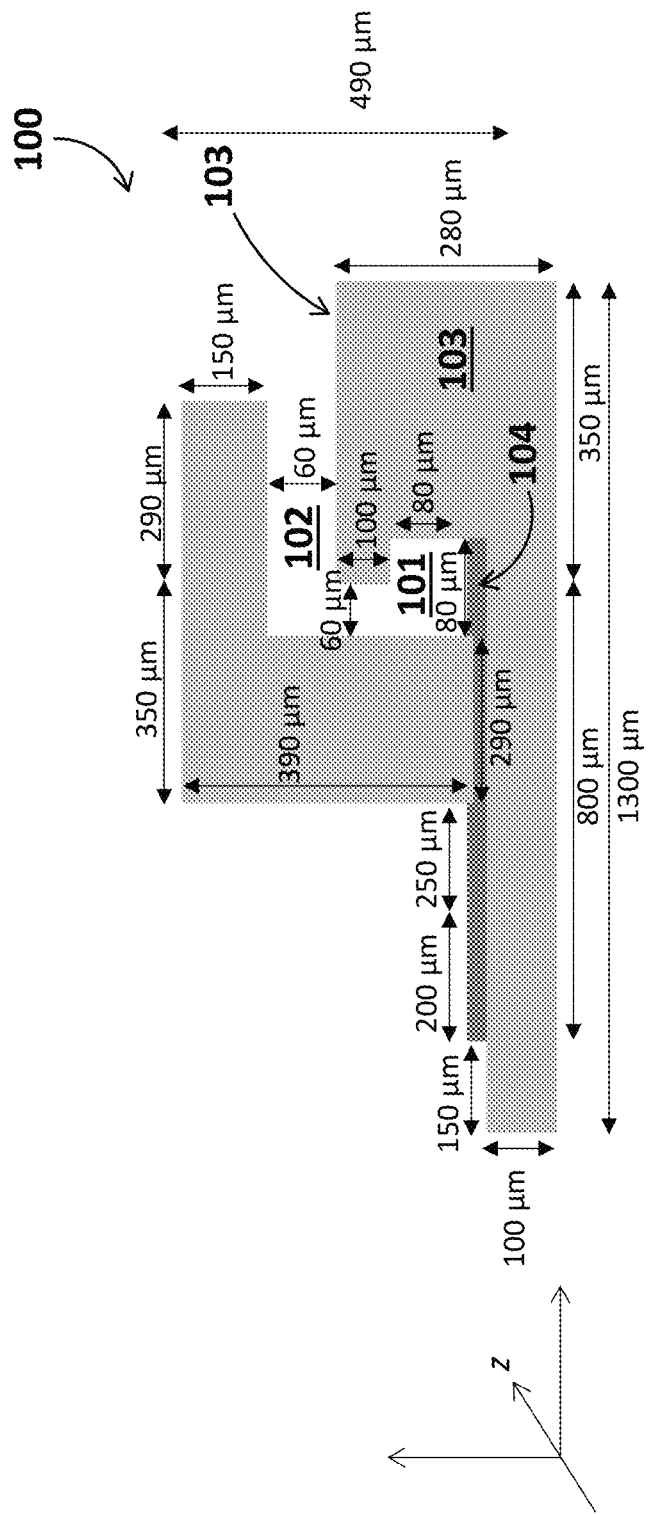
FIG. 1B is a profile view of the schematic representation of a neuromodulation device shown in FIG. 1A. The perspective is indicated by the axes. Figure may not be to scale.
Figure 1C:
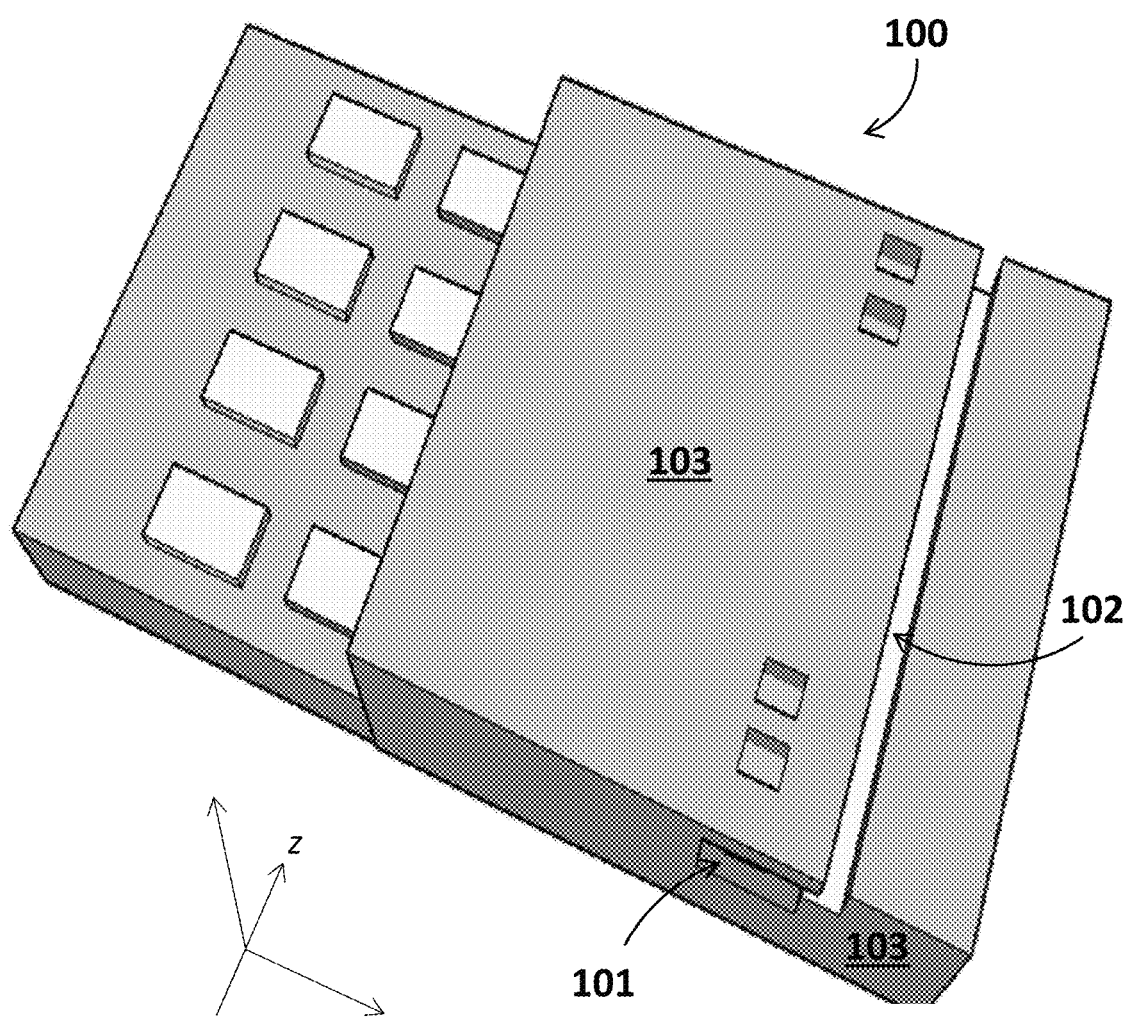
FIG. 1C is a top perspective view diagram of a neuromodulation device described herein.

Embodiments described herein can be understood more readily by reference to the following detailed description and examples. Methods, devices, and features described herein, however, are not limited to the specific embodiments presented in the detailed description and examples. It should be recognized that these embodiments are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 and ending with a maximum value of 10.0 or less, e.g. 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the endpoints 5 and 10.

Further, when the phrase "up to" is used in connection with an amount or quantity, it is to be understood that the amount is at least a detectable amount or quantity. For example a material present in an amount "up to" a specified amount can be present from a detectable amount and up to and including the specified amount.

I. Neuromodulation Devices

In one aspect a neuromodulation device 100 is described herein, which in some embodiments, comprises a chamber 101 operable to receive a nerve 200, at least one electrode 104 disposed in the chamber 101, and a channel 102 defined by two walls. In some embodiments, a channel 102 can be in fluid communication with an interior of the chamber 101 and an external surface 103 of the device 100. In some instances, a channel 102 can be in fluid communication with more than one external surface 103 of the device 100. In some embodiments, the channel 102 comprises an average width that is 10-50% smaller than an average diameter of the chamber 101. In some instances, the channel 102 can be non-linear Devices described herein can be formed from a polymer. For example, in some embodiments, a neuromodulation device can be fabricated using flexible polyimide/SiC substrates with gold metallization in ultra-micro scale using established thin-film methods. In some embodiments, a device can be made of SU-8 or other such polymer, using commonly employed microfabrication methods and photoresist techniques.

In some embodiments, a device described herein can be conductive. For example, a device can be connected to an electrical pulse generator and/or an electrical stimulator. The device, in some cases, can comprise transmission circuitry. For example, transmission circuitry of a device can facilitate magnetic inductive coupling.

Now turning to specific components of a device 100, in some embodiments, a chamber 101 can be a recording chamber 101 and/or a stimulating chamber 101. For example, a recording chamber 101 can record electrical activity within the chamber 101 and a stimulating chamber 101 can elicit an electrical stimulus within the chamber 101.

In some embodiments, a chamber 101 is operable to receive a nerve 200. In some embodiments described herein, a nerve 200 is also a target nerve 200. A nerve 200, as described herein, can include a single nerve axon, multiple nerve axons, a nerve fiber, a nerve bundle, a nerve fascicle, or other similar neuroanatomical structure. It should be understood, that a nerve 200, as described herein, should be a functionally intact nerve. For example, a functionally intact nerve should comprise a functional pre- and post-synaptic terminal and should be functionally capable of propagating an action potential. A nerve, in some embodiments, can have an average diameter of at least 50 μm, at least 100 μm, at least 200 μm, at least 300 μm, at least 400 μm, at least 500 μm, at least 600 μm, at least 700 μm, at least 800 μm, or at least 900 μm. In some embodiments, a nerve can have an average diameter between about 50 μm and 1 mm or between about 50 μm and 800 μm.

A chamber 101, in some embodiments, can be cylindrical in shape, as in a pipe, wherein the ends of a cylindrically shaped chamber 101 are open to allow longitudinal exit of a nerve 200 from the chamber 101 toward the pre- and post-synaptic terminals of the nerve 200. Whereas a cylinder comprises a circular shape, it should be understood that a chamber 101 can also comprise a triangular, square, pentagonal, hexagonal, or polygonal shape having n number of sides, while maintaining a general 3-dimensional structure resembling a cylinder, or a pipe, having open ends and operable to receive a nerve 200.

A chamber 101, in some embodiments, can be in fluid communication with a first external surface 103 and a second external surface 103 of a device 100, wherein the first and second external surfaces 103 are on opposite sides of the device 100 and the chamber 101, positioned between the first and second external surfaces is in fluid communication with each opposing first and second external surfaces 103 of the device 100.

A chamber 101, in some embodiments, comprises a length, width, and depth, wherein the length of the chamber 101 corresponds to a z-axis that traverses longitudinally along a nerve 200 extending through the device 100. In some embodiments, a chamber 101 can have an average length of at least 10 µm. In some embodiments, a chamber 101 can have an average length of at least 50 µm, at least 100 µm, at least 500 µm, or at least 1000 µm. In some embodiments, a chamber 101 can have an average length of between about 10 µm and 10 mm. In some embodiments, a chamber 101 can have an average length of between about 10 µm and 5 mm, between about 10 µm and 3 mm, between about 10 µm and 1 mm, or between about 10 µm and 1 mm.

The width and depth of a chamber 101, in some embodiments, correspond to cross-sectional dimensions of an x-y-plane orthogonal to the z-axis of the chamber 101. For example, a cylindrically shaped chamber 101 can have a width and depth corresponding to a diameter of the chamber 101. The diameter of a non-cylindrically shaped chamber 101 can be measured by averaging the distance of measurements intersecting the center point of a cross-section of the chamber 101, wherein the center point is positioned on the z-axis extending through the middle of the chamber 101. In some embodiments, a chamber 101 can have an average diameter of about less than 10 mm. In some embodiments, a chamber 101 has an average diameter of about 0.5 µm to about 5000 µm, about 0.5 µm to about 4000 µm, 0.5 µm to about 3000 µm, about 0.5 µm to 2000 µm, about 0.5 µm to 1000 µm, about 0.5 µm to 900 µm, or about 0.5 to 800 µm, or about 0.5 µm to 500 µm.

In some embodiments, a chamber 101 has an average diameter that is substantially the same as the average diameter of a target nerve 200. In some embodiments, the average diameter of the chamber 101 is no more than 5% larger or no more than 5% smaller than the average diameter of the target nerve 200. In some embodiments, the average diameter of the chamber 101 is no more than 15% larger or no more than 15% smaller than the average diameter of the target nerve 200. For example, for a target nerve 200 having an average diameter of about 80 µm, a device 100 can have an average diameter of no less than about 56 µm, and no more than 104 µm. In some embodiments, a chamber 101 has an average diameter that is about 80-120% of a target nerve 200, about 85-115% of a target nerve 200, about 90-110% of a target nerve 200, about 95-105% of a target nerve 200, or about 100% or equal in size of a target nerve 200.

In some embodiments, a device 100 described herein comprises a channel 102 defined by two walls. The two walls can provide an upper boundary and lower boundary of a channel described herein. In some instances, a distal end of a channel 102 can be in fluid communication with an interior of a chamber 101 and a proximal end of a channel 102 can be in fluid communication with an exterior surface 103 of a device 100. Thus, a distal end of a channel 102 is open to a chamber 101. In some embodiments, the chamber 101 is indefinitely or constantly open to the channel 102, such that the distal opening of the channel 102 into the chamber 101 does not close. Moreover, a channel 102 can connect the interior of a chamber to an external surface 103 of a device 100 described herein. Thus, the chamber 101 is essentially in constant communication with an exterior surface 103 of the device via the channel 102. For example, the chamber 101 remains open to the channel at all times and the channel 102 remains open to an exterior surface at all times.

A channel 102, in some embodiments, comprises a length, a depth, and a diameter, which are not interchangeable. Similar to the length of a chamber 101 described above, a length of a channel 102 corresponds to a measurement along a z-axis, which traverses longitudinally along a nerve 200. A length can be measured at any point along a channel 102 between the distal end of channel opening into a chamber 101 and the proximal end of a channel opening to an exterior surface 103 of the device. In some embodiments, a distal end of a channel 102 can be in fluid communication with a chamber 101 for an entire length of the chamber 101. In some cases, the average length of a channel 102 is substantially the same as the average length of a chamber 101 of a device 100 described herein.

In some embodiments, a channel 102 can have an average length of at least 10 µm. In some embodiments, a channel 102 can have an average length of at least 50 µm, at least 100 µm, at least 500 µm, or at least 1000 µm. In some embodiments, a channel 102 can have an average length of between about 10 µm and 10 mm. In some embodiments, a channel 102 can have an average length of between about 10 µm and 5 mm, between about 10 µm and 3 mm, between about 10 µm and 1 mm, or between about 10 µm and 1 mm.

The depth of a channel 102 corresponds to a distance measured between the distal opening and the proximal opening of the channel 102, wherein the distance is measured along an imaginary centerline positioned equidistant between each channel wall. In some cases, a depth can be a linear measurement. For example, in some cases, the channel 102 is a linear channel 102. In other cases, a channel 102 can be non-linear, wherein a non-linear channel comprises one or more turns, curves, or bends in the channel walls. Thus, in some instances, the depth of a non-linear channel 102 can be measured by measuring the distance along the imaginary centerline of a channel 102 between the distal opening and proximal opening of the channel 102, and along each bend in the non-linear channel 102. For example, in some embodiments, a channel 102 can comprise an "L" shape, such that the channel 102 depth measurement comprises a 90-degree turn and each end of the "L" corresponds to the distal and proximal openings of the channel. In an exemplary channel having a 90-degree turn, the depth can be measured by summing the distance of an imaginary centerline of the channel for each arm in the "L" of the channel 102 extending between the proximal opening and the distal opening of the channel 102 to where the imaginary lines of each arm meet.

In some embodiments, a channel 102 can have an average depth of between about 50 µm and 10 mm. In some embodiments a channel 102 can have an average depth of between about 50 µm and 5 mm, between about 50 µm and 1 mm, between about 50 µm and 900 µm, between about 50 µm and 800 µm, between about 50 µm and 700 µm, between about 50 µm and 600 µm, between about 50 µm and 500 µm, between about 50 µm and 400 µm, between about 50 µm and 300 µm, between about 50 µm and 200 µm, or between about 50 µm and 100 µm.

The diameter of a channel 102 corresponds to a measurement of the channel 102 positioned in an x-y plane that is orthogonal to the z-axis, as described above. A diameter of a channel 102 can be a constant, such that the diameter of a channel 102 does not change between the proximal opening and distal opening of the channel 102. That is, in some embodiments, a diameter of a channel 102 comprises less than 10% variability of an average diameter across an entire depth of a channel 102. In some cases, a channel 102 comprises less than 5% variability, less than 3% variability, or less than 2% variability of an average diameter along an entire depth measurement of a channel 102. In some cases, a diameter can be determined by measuring the shortest distance between the two walls of a channel 102.

A diameter of a channel 102, in some embodiments, is less than a diameter of a target nerve 200. For example, in some embodiments, a channel 102 diameter can be at least 5% smaller than a diameter of a target nerve 200. In some embodiments, a channel 102 diameter can be at least 5%, at least 10%, at least 15%, at least 20%, at least 25%, at least 30%, at least 35%, at least 40%, at least 45%, or at least 50% smaller than a diameter of a nerve 200. In some embodiments, a channel 102 diameter can be no more than 60% smaller than a target nerve 200 diameter. In other embodiments, a channel 102 diameter can be no more than 50% smaller than a target nerve 200 diameter. In some embodiments, a channel 102 diameter can be between about 5% and 60% smaller than a diameter of a target nerve 200. In some cases, a channel 102 diameter can be between about 10% and 50%, between about 10% and 40%, between about 15% and 40%, between about 20% and 35%, or between about 20% and 40% smaller than a diameter of a target nerve 200.

Furthermore, similar to a chamber 101 described hereinabove, a channel 102 described herein can have open ends in fluid communication with the open ends of the chamber 101 such that a nerve 200 can be inserted into a chamber 101 by sliding, moving, or inserting a longitudinal section of a nerve 200 into a chamber 101 via a channel 102. Thus, in some instances, a channel 102 described herein is operable to receive a nerve 200, including a target nerve 200. Moreover, in some embodiments, a channel 102 can be in fluid communication with at least three external surfaces 103 of the device 100. For example, a channel 102 can be open to an interior of a chamber 101 at a distal end of the channel and the channel can extend along a depth of the channel to a third external surface 103 at a proximal end of the channel, while maintaining fluid communication with a first external surface 103 and a second external surface 103 on opposing sides of the device 100 corresponding to opposing ends of the z-axis.

In some embodiments, a device described herein comprises at least one electrode 104 disposed within a chamber 101 of the device. An electrode 104 can include various types of electrodes, including flat electrodes or thin film electrodes or needle electrodes. A thin film electrode disposed in the chamber can have a recording or stimulating surface within 100 μm or within 50 μm of an outer surface of a nerve 200 disposed in the chamber 101. A needle electrode disposed in the chamber can have a needle shaped recording and/or stimulating surface that can penetrate a surface of a nerve 200 disposed in the chamber 101. An electrode that penetrates a nerve disposed in the chamber 101 can stimulate and/or record intraneurally, which can provide greater selectivity and/or resolution when recording and/or stimulating. Additionally, an electrode 104 can be positioned on any surface within the chamber 101, including a top, a bottom, or side surface of the chamber.

In some embodiments, a plurality of electrodes can be disposed within a chamber. Wherein more than one electrode is present in the chamber, a combination of electrode types can be used. For example, both flat electrodes and/or needle electrodes can be used in a recording and/or stimulating chamber 101. A device described herein can comprise mono-polar, bi-polar, tri-polar, or a multi-electrode array electrodes. In some cases, a plurality of electrodes can be configured in a tripolar configuration. Such a tripolar configuration can provide improved nerve specificity and/or selectivity while simultaneously reducing extraneous biological noise.

In some embodiments, an electrode can be made from one or more conductive metals. For example, in some instances, an electrode comprises gold, titanium nitride (TiN), iridium oxide (IrO), iridium, carbon nanotubes, graphene, and/or platinum (Pt). An electrode, in some instances, can have a charge injection capacity of about 0.1 mC/cm$^2$ or greater. Further, in some embodiments, an electrode described herein can be a wired or a wireless electrode. A wireless electrode can comprise a wireless integrated circuit within the device 100.

In some embodiments, an electrode can comprise a stimulating and/or recording surface area of between about 25 μm$^2$ and 25 mm$^2$. In some instances, an electrode comprises a stimulating and/or recording surface area of between about 100 μm$^2$ and 1 mm$^2$ or between about 100 μm$^2$ and 0.5 mm$^2$.

II. Methods of Neuromodulation

In another aspect, methods of treating and/or preventing perineal dysfunction are disclosed herein, which in some embodiments, comprises neuromodulating one or more pelvic floor muscles. Some exemplary pelvic floor muscles include the cremaster muscle, bulboglandularis muscle (Bgm), ischiocavernosus muscle, bulbospongiosus muscle (Bsm), pubococcygeus muscle (Pcm), iliococcygeus muscle (Icm), coccygeus muscle, or puborectalis muscle. In some embodiments, a pelvic floor muscle can be neuromodulated or stimulated simultaneously or independently of one or more other pelvic floor muscles. In some cases, neuromodulating one or more pelvic muscles comprises modulating one or more pelvic nerves. In some instances, a pelvic nerve can include any nerve, nerve bundle, nerve fascicle, or nerve tract that innervates a pelvic floor muscle. For example, in some cases, the nerve can be a cremaster nerve, bulboglandularis nerve, ischiocavernosus nerve, bulbospongiosis nerve, pubococcygeus nerve, iliococcygeus nerve, coccygeus nerve, or puborectalis nerve. By neuromodulating one or more nerves innervating one or more pelvic floor muscles, methods described herein provide greater specificity and resolution of pelvic floor muscle stimulation.

It should be understood than any device described hereinabove in Section I can be used in methods described herein. For example, the device 100 described hereinabove, comprises a chamber operable to receive a nerve, such as a nerve innervating a pelvic floor muscle. In some cases, multiple devices 100 can be used to perform a method described herein. For example, two or more devices 100 can be used to stimulate two or more pelvic floor muscles. Furthermore, since a device 100 described hereinabove can record and/or stimulate, two devices can be used on the same pelvic floor muscle to independently record and stimulate, or one device can be used to record and stimulate the pelvic floor muscle.

Now turning to specific steps of a method, in some embodiments, a method described herein can comprise disposing a first nerve in a first device, the first device 100 comprising a chamber, at least one electrode disposed in the chamber, and a channel defined by two walls, and selectively stimulating the first nerve by sending electrical signals from an electrode of the first device to the first nerve.

In some embodiments, a method further comprises disposing a second nerve in a second device, the second device comprising a chamber, at least one electrode disposed in the chamber, and a channel defined by two walls, and selectively stimulating the second nerve by sending electrical signals from an electrode of the second device to the second nerve, wherein the first nerve is a bulbospongiosus nerve and the second nerve is a pubococcygeus nerve.

Selectively stimulating, as described herein, can mean stimulating a specific target nerve, and only the specific target nerve, such as a motor neuron that innervates a muscle. For example, non-selective stimulation can result in non-selective muscle stimulation, wherein multiple muscles are simultaneously stimulated from a single electrical signal sent from an electrode to a nerve. For example, stimulation of a sacral nerve root, while being a single nerve can, stimulate multiple muscles from a single electrical signal sent from an electrode to the nerve. In contrast, selectively stimulating results in finer resolution wherein only one muscle is stimulated from an electrical signal sent from an electrode.

In some embodiments, a method can comprise disposing or implanting any device 100 described hereinabove in Section I into a subject. In some instances, the subject can be in need of pelvic floor muscle simulation. Implanting a device can be achieved by disposing or positioning a target nerve 200 within a chamber 101 of the device 100 and stimulating the nerve 200 disposed within the chamber. A target nerve 200 can include any section of a functionally intact nerve 200, as described hereinabove in Section I. In some embodiments, a target nerve innervates a pelvic floor muscle. For example, the bulbospongiosus nerve (Bsn) and/or the pubococcygeus nerve (Pcn) can be target nerves 200 of a method described herein.

In some embodiments, implanting a device 100 can comprise longitudinally stretching a section of a nerve 200 and transversely sliding the stretched nerve through the channel into a chamber. Stretching a nerve 200 can comprises stretching the nerve 200 for less than 30 seconds or less than 10 seconds to reduce the average diameter of the stretched section of the nerve 200. In some cases, the stretched nerve can have an average diameter that is 5% to 50% smaller than the average diameter of the same nerve at an unstretched section. In some cases, the stretched nerve can have an average diameter that is 5% to 40%, 5% to 35%, 5% to 30%, 5% to 25%, 5% to 20%, 5% to 15%, or 5% to 10% smaller than the average diameter of the same nerve at an unstretched section.

In some cases, a method further comprises positioning an electrode into a recording and/or stimulating position. For example, in some cases, positioning an electrode comprises piercing, puncturing, or penetrating the surface of the nerve with the electrode, such that the electrode is in an intraneural recording position and/or an intraneural stimulating position. In some cases, positioning an electrode comprises positioning an electrode within 100 μm or within 50 μm of the external surface of a nerve 200. For example a thin film electrode can be positioned within 100 μm or within 50 μm of the external surface of a nerve 200.

In some embodiments, a method described herein comprises electrically stimulating one or more pelvic muscle nerves. For example, electrical stimulation can be provided via one or more devices 100 described herein. In some cases, electrical stimulation can be provided in pulses. An electrical stimulation pulse, in some embodiments, can be between about 1 microsecond and 1 second in duration. In some embodiments, an electrical stimulation pulse can be between about 1 μs and 500 millisecond (msec), between about 1 μs and 100 msec, between about 1 μs and 50 msec, between about 1 μs and 40 sec, between about 1 μs and 30 msec, between about 10 μs and 20 msec, or between about 100 μs and 5 msec.

Additionally, in some embodiments, electrical stimulation can be provided in a dose comprising multiple pulses, wherein each electrical stimulation pulse is provided after a period of rest or a period of no electrical stimulation. In some cases, the period of rest or no stimulation in between each electrical stimulation pulse can be a constant time duration. In other cases, the period of rest or no stimulation in between each electrical stimulation pulse can vary in time duration, such that the rate of electrical stimulation pulse can be constant, increase, or decrease over time in a single dose. For example, in some embodiments, electrical stimulation pulses can be provided at a rate of about 1 to 200 pulses per second, about 1 to 100 pulses per second, about 1 to 50 pulses per second, or about 1 to 20 pulses per second.

In some embodiments, electrical stimulation can be provided to a nerve at a frequency of between about 1 Hz and 500 KHz. In some embodiments an electrical stimulation can be provided to a nerve at a frequency of between about 1 Hz and 400 KHz, between about 1 Hz and 300 KHz, or between about 1 Hz and 200 KHz.

In some embodiments, an electrical stimulation pulse provides a current to the target nerve of between about 1 μAmp and 5 Amp. In some embodiments an electrical stimulation pulse provides a current to the target nerve of between about 1 μAmp and 3 Amp, between about 1 μAmp and 2 Amp, or between about 1 μAmp and 1000 milliAmp.

In some instances a dose of electrical stimulation can have a defined time duration. For example, in some embodiments, a dose can be between about 1 second and 10 minutes. A dose, in some embodiments, can be between about 10 seconds and 10 minutes, between about 10 seconds and 1 minute, or between about 10 seconds and 30 seconds. In some embodiments, multiple doses can be provided over the course of a treatment or prevention paradigm. For example, one or more doses can be provided on a daily, weekly, or monthly schedule.

Many modifications and other embodiments of the subject matter will come to mind to one skilled in the art to which the subject matter pertains having the benefits of the teachings presented in the foregoing descriptions and the associated drawings. For example, although specific configurations of neuromodulation devices are described above and depicted in the figures, numerous other neuromodulation devices configured to modulate a nerve may benefit from embodiments of the present subject matter. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Various implementations of devices and methods have been described, and exemplary embodiments are described below in fulfillment of various objectives of the present disclosure. It should be recognized that these implementations are merely illustrative of the principles of the present disclosure. Numerous modifications and adaptations thereof will be readily apparent to those skilled in the art without departing from the spirit and scope of the present disclosure. For example, individual steps of methods described herein can be carried out in any manner not inconsistent with the objectives of the present disclosure, and various configurations or adaptations of devices described herein may be used.

Example 1

Design of a Device for Neuromodulation

The present example illustrates the design and fabrication of an exemplary device 100, sometimes referred to as a "Neuroclip", according to one or more embodiments disclosed herein. The exemplary device can be implanted onto small caliber nerves and nerve fibers. The multi electrodes 104 grouped in tripolar configuration can provide specificity and selectivity.

The disclosed approach is drastically different than prior approaches in that a device 100 described herein uses a slide-n-lock mechanism to place and secure the electrode 104 of the device 100 onto the nerve 200. The electrode has an L-shaped slit through which the target nerves slide and lock into a recording/stimulating compartment or chamber 101.

The slide-in-lock mechanism is unique and particularly beneficial for inserting the electrode onto small nerves with minimal handling and reducing the risk of nerve damage.

A slit opening of proximal channel 102 can be on either the top or to the side of the device 100. The channel is calculated to be about 25-50% smaller than the nerve diameter through which a nerve 200 can be inserted via a soft and brief stretching of the nerve tissue, and then release inside an electrode chamber 101.

This device 100 provides a self-securing mechanism of the nerve without damaging it, as well as reducing the time and effort required for implantation (see FIG. 1). As shown in FIG. 1A-1B, a device 100 can have tripolar (3) gold electrode contact pads or 8 gold electrode pads. Furthermore, a device 100 can have a channel that interfaces with a top-side of the device 100, such that the device 100 comprises a top-insertion mechanism for a nerve 200. As shown in FIG. 1C, an actual device 100 prototype was fabricated using an SU-8 photoresist and having a tripolar electrode with a side-insertion channel. The device's 100 impedance at 1 kKz was around ~500 KOhms across two gold electrodes. Such exemplary devices 100 provide improved safety and reliable of a neuromodulation device 100 that can be customized to targeted nerve 200 anatomy.

Extensive clinical studies of stress and strain on peripheral nerves resulted in an accepted values of 20-32% elongation to avoid structural and mechanical damage. It has also been shown that effects on electrical conductivity at a transient 5-10% strain could be recovered immediately with no apparent functional deficits.

Figure 2:
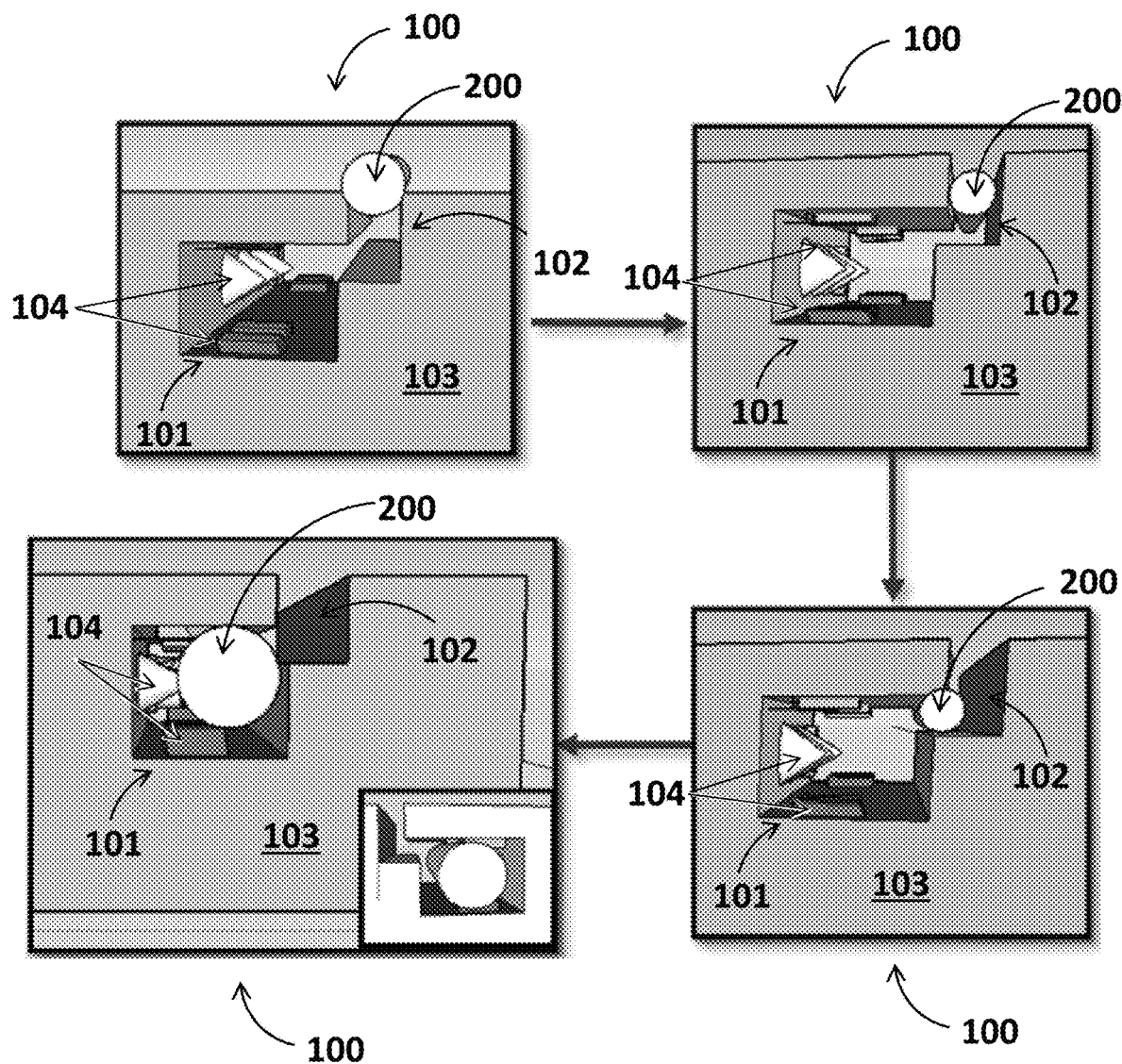
FIG. 2 is a profile view schematic of a device described herein receiving a nerve.

FIG. 2 illustrates the steps of implantation of the so called "NeuroClip" electrode (an exemplary embodiment of the present disclosure) through the innovative slide-n-lock method. Target nerves 200 slide longitudinally into an opening or channel with an internal diameter 25% less than the inserted nerve 200 diameter, transiently undergoing a minimal elongation longitudinally and compression transversely.

Additionally, some embodiments of a device 100 include extended features as to provide either a top, bottom or side access to the nerve 200. FIG. 2 shows an example embodiment having a simple "L-shaped" channel to enhance the locking mechanism with minimal additions to the design architecture.

Example 2

Fabrication of a Device for Neuromodulation

A neuromodulation device (a "Neuroclip version I") was fabricated at using flexible polyimide/SiC substrates with gold metallization in ultra-micro scale for intraneural electrode features with two sets of tripolar extraneural iridium oxide electrodes using established thin-film methods. Thin-film fabrication techniques provide the unique opportunity to miniaturize the electrode design to accommodate the small caliber neural interfacing. The multi electrodes grouped in tripolar configuration not only provide specificity and selectivity but also reduce the effective biological noise components. Further we also describe a wireless option with a wireless integrated circuit added to the NeuroClip electrode in a two-layered device integration and encapsulation.

Figure 1D:
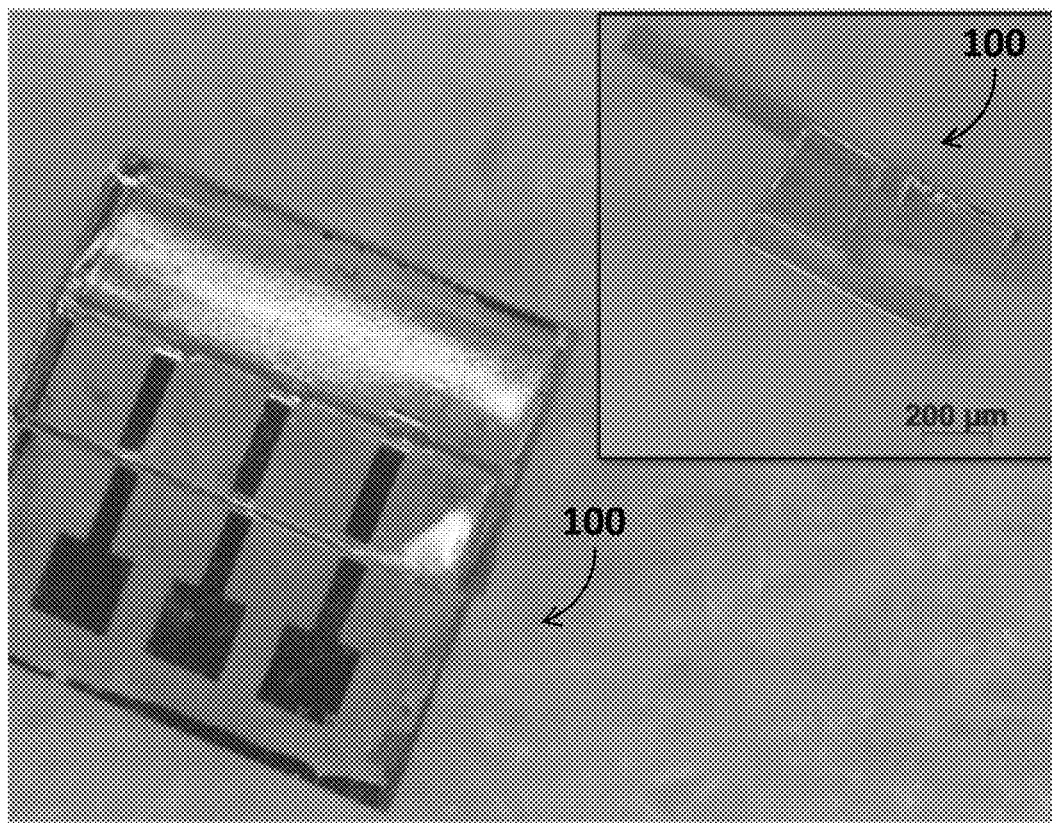
FIG. 1D is a photograph of a neuromodulation device.
Figure 1E:
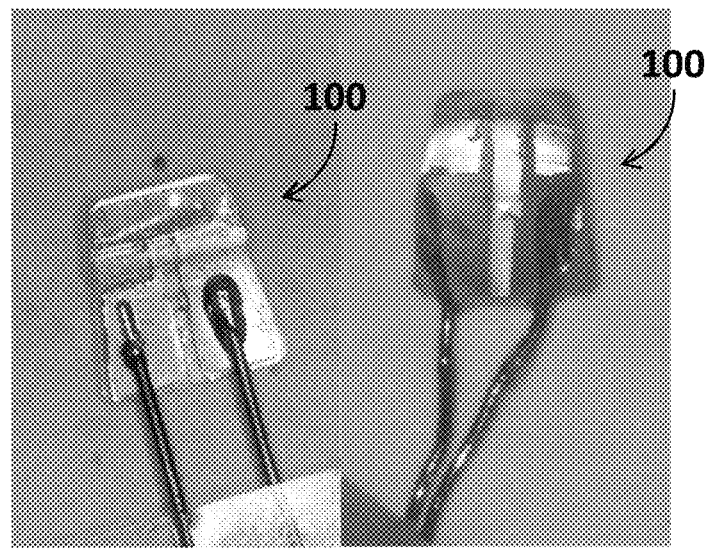
FIG. 1E is a photograph of a neuromodulation device.

Functional devices were fabricated with Sub to test the slide-n-lock mechanism of neural implantation approach. FIG. 1D shows the Sub NeuroClip electrode layout schematics. The electrodes were then fabricated in collaboration with MiNDS lab, UTD (Micro/Nano Devices and Systems), adapting previously described steps. Post-fabrication and UV sterilization for 30 minutes, the NeuroClip was implanted onto the Glossopharyngeal rootlet to test the slide-n-lock mechanism (FIG. 1E). Additionally, when compared with the commercially available microcuff electrodes, the time, and steps involved with implantation have significantly reduced.

Example 3

Fabrication of a Device for Neuromodulation

Figure 3A:
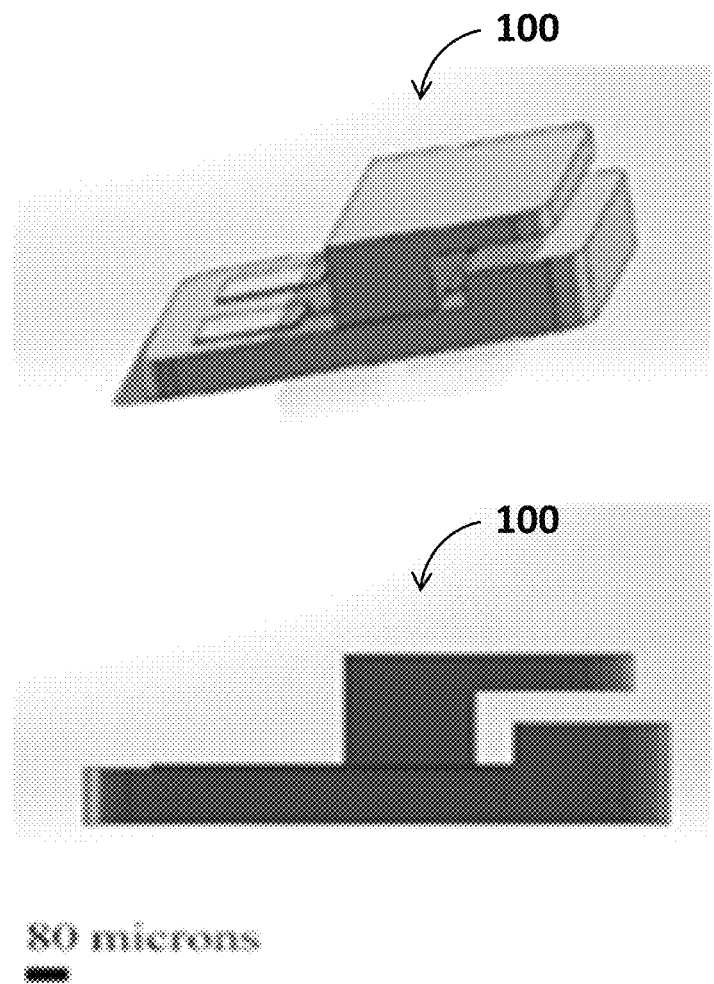
FIG. 3A is a schematic representation of a neuromodulation device described herein.
Figure 3B:
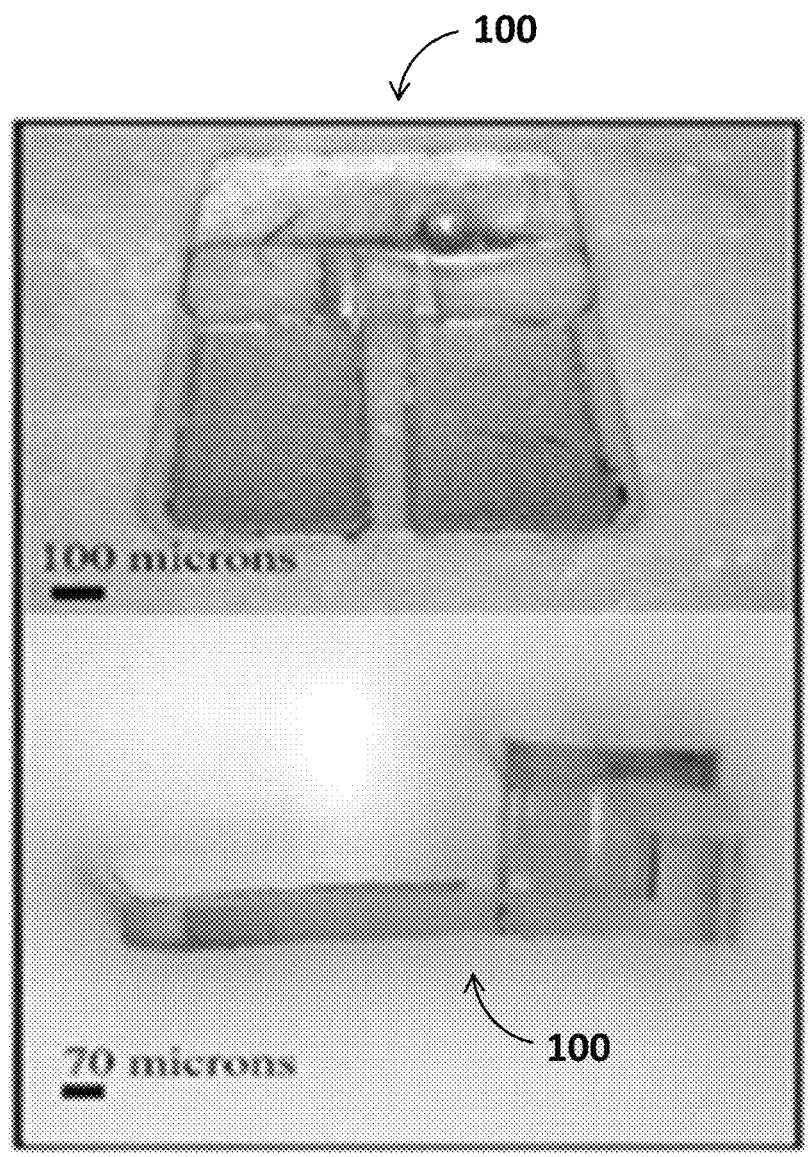
FIG. 3B is a photograph of a neuromodulation device.
Figure 3C:
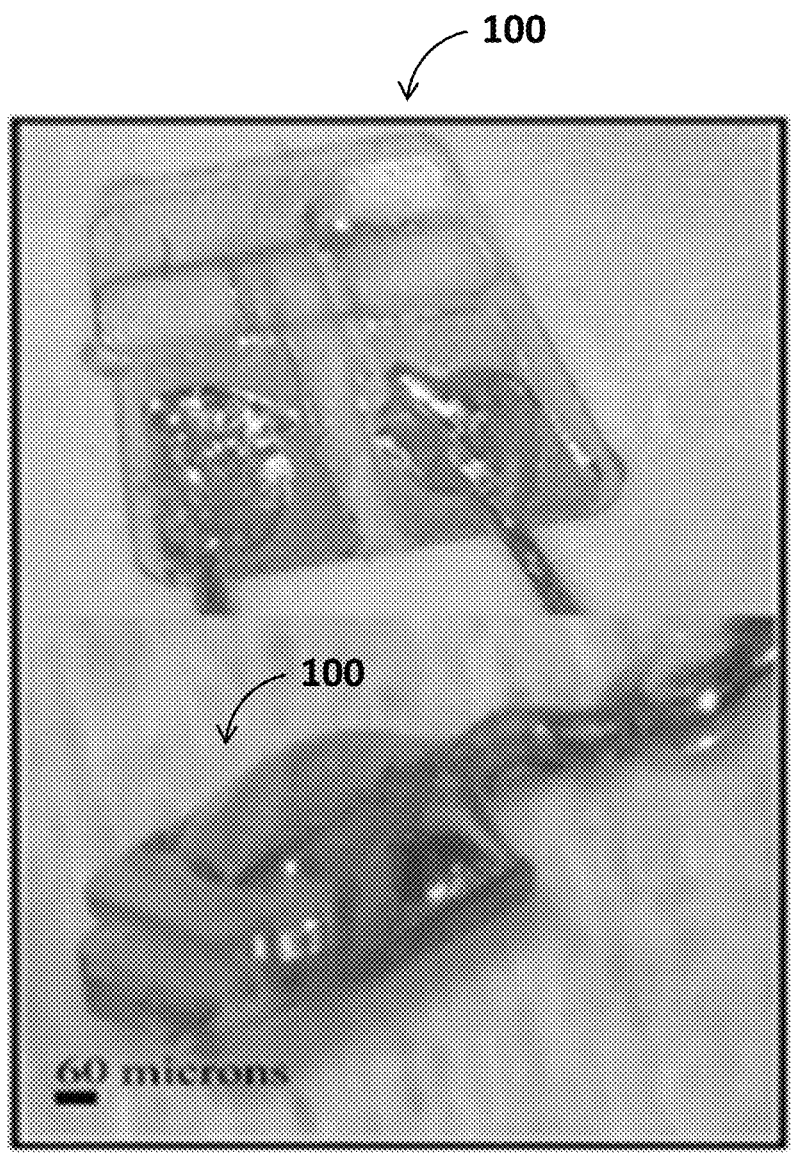
FIG. 3C is a photograph of a neuromodulation device.
Figure 4:
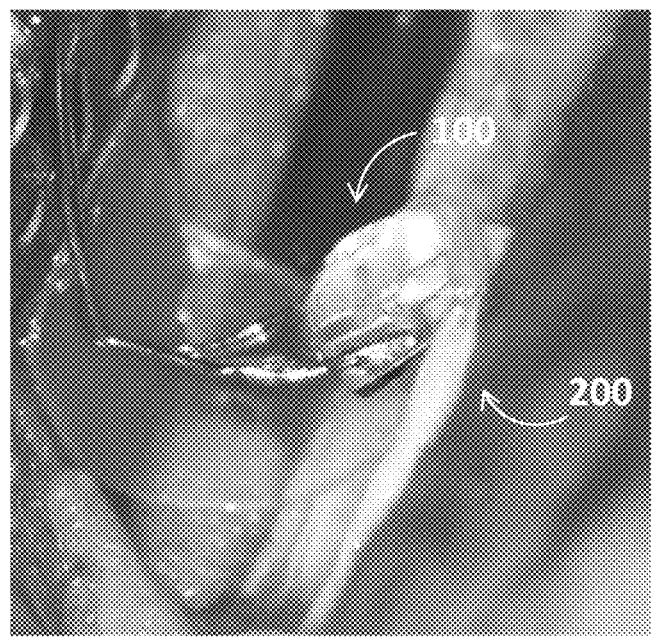
FIG. 4 is a wired neuromodulation device, as described herein, having a 100-200 micrometer fascicle of a rat deep peroneal nerve disposed in the chamber.
Figure 4:
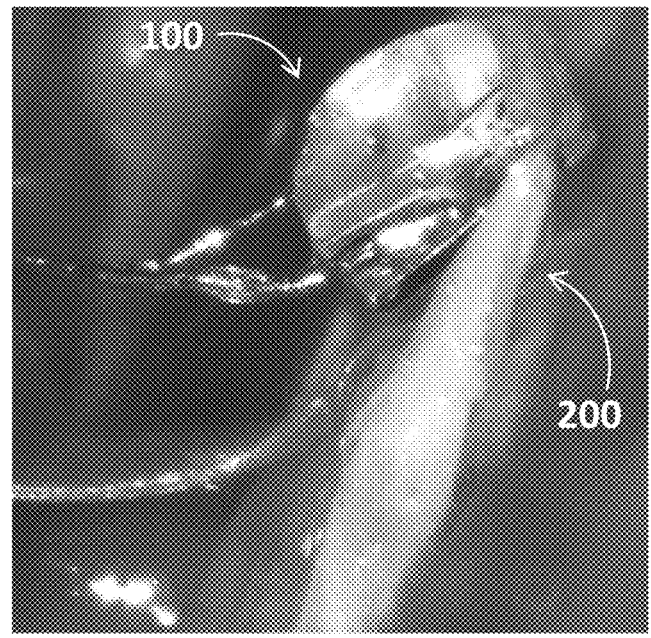

A second version of a neuromodulation device ("Neuro-Clip version II") was fabricated similar to the version I except for the number of electrode contacts. FIG. 4 shows the Su-8 fabricated NeuroClip V2. Version II comprises curved corners and cantilever structures for one channel slide-n-lock mechanism (FIG. 3).

Prior to implantation, the NeuroClip's were characterized in-vitro to evaluate the electrochemical impedance. The devices were placed in phosphate buffered saline and a 3 cell electrochemical cell was formed using an Ag—AgCl reference electrode and Pt wire counter electrode. The typical impedance spectroscopy was obtained using the Gamry Potentiostat (GamryInstruments). Impedance at 1 kKz was around ~500 KOhms across two electrodes.

Example 4

Functional Testing of Neuromodulation Device In Vivo

Acute testing of a neuromodulation device having embodiments described herein was carried out in adult Female Sprague Dawley rats weighing up to 500 grams. The animals were anesthetized with inhaled isoflurane (1-3%) from a vaporizer with scavenger system. The appropriate level of anesthesia was confirmed by the lack of response to noxious stimuli. Animals were kept under anesthesia throughout the experiments, body temperature was maintained with heating pads, and each rat's condition was monitored continuously via a pulse oximeter on the extremities.

The left hind limb deep peroneal nerve was exposed and the dorsal fascicle was teased out gently with the help of glass rods. The teased fascicle was then placed and secured into the microchannel of the NeuroClip using the slide and lock mechanism. FIG. 4 shows the device 100 attached to a 100 micrometer fascicle of the rat peroneal nerve 200. All animal procedures were performed in accordance with the guidelines of the Institutional Animal Care and Use Committees of the University of Texas at Dallas.

The nerves were then stimulated using an AM systems Stimulator (A-M Systems). Animals were kept under anesthesia throughout the experiment and body temperature was maintained with heating pads and its condition was simultaneously monitored continuously via a pulse oximeter on the extremities. The animals were placed prone to allow for an uninterrupted video recording of foot and toe movement using hardware and software solutions provided by Cineplex Behavioral Research System (Plexon Inc.). Videos were acquired at 80 frames per second. Individual electrodes were stimulated with a gradual increase in the current 1 mA to 2 mA to identify the threshold currents at which a visible isometric twitch was observed. Charge-balanced constant-current rectangular pulses (1 ms duration, 2 Hz) were used to evaluate the toe kinematics. Toes were painted with animal safe dyes for color-based tracking. With appropriate hue, contrast and saturation adjustments, the individual dye contours were identified in Cineplex. The geometric centroid of the dyed region was then tracked in the x-y plane, and was used to compare and contrast the tor recruitment patterns with respect to increase in stimulus current.

Figure 5:
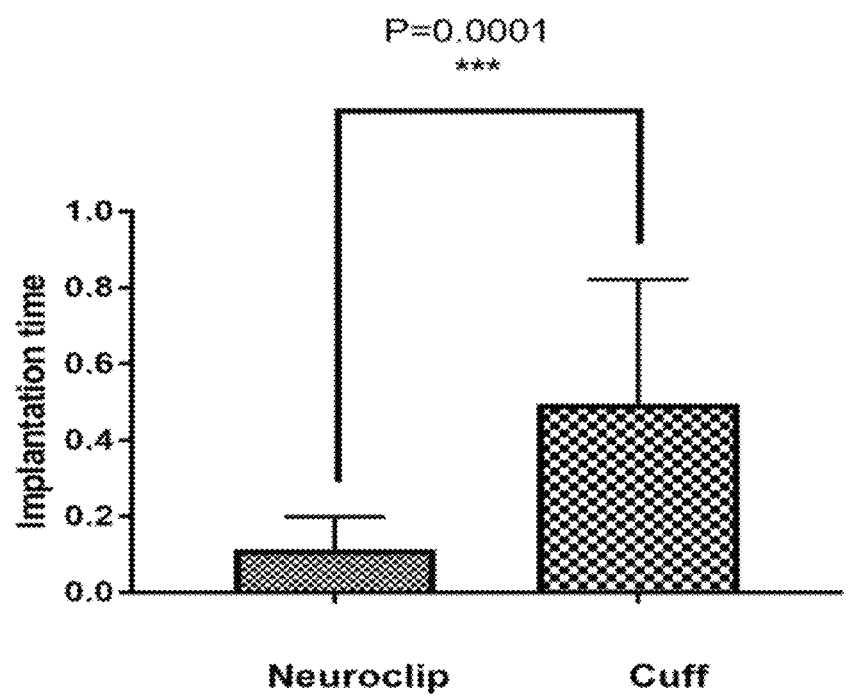
FIG. 5 is a bar graph illustrating implantation of time of neuromodulation devices.

The amount of time required for implantation of the neuroclip compared to placing a standard cuff electrode was tested in these small nerves by two independent surgeons with no prior experience in either method. Post exposure of DPN fascicle, cuff electrode (diameter 100 μm) and neuroclip were implanted alternatively in the exposed fascicle. The procedure was recorded by surgical camera. This was repeated 7 times. The time of implantation was calculated from the recorded video by means of activity tracking. FIG. 5 shows timing of implantation in the DPN fascicle for neuroclip (dia~80 μm) and cuff electrode (dia~100 μm indicating that the time of implantation of neuroclip is significantly less (p=0.0001). The neuroclip reduced up to 90% the time, and therefore, handling required to place electrodes in these small nerves of nerve fibers. Further, surrounding anatomy was only minimally manipulated within the time frame, thus providing small implantation window and reducing the possibility of tissue damage.

The implanted fascicle in the neuroclip was stimulated with constant voltage cathodic first biphasic electrical stimulation of 1 ms long charge-balanced pulses at 2 Hz frequency. Electromyograms (EMG) were recorded from the Tibilias anterior muscle using needle electrodes. The stimulation pool of five voltages was selected by way of increasing the amplitudes by 0.1 mV from the recorded threshold amplitude. The experiment was repeated for three trials with every trial consisting of randomized amplitude testing blocks from the stimulation pool. The stimulation was carried out for a period of 30 secs with a 1 min rest time between varying stimulation amplitudes. The rest duration between consecutive trials was 5 mins to overcome muscle fatigue and residual effects from previous stimulation trials.

The electrochemical characterization across 7 electrodes gave an average impedance value of 250.63±53.42KΩ at 1 KHz frequency. The charge storage capacity was calculated from the CVs. The cathodic charge storage capacity had an average value of 0.231±0.12 mVcm-2 and the average charge per phase reported was 0.65±0.20 nC.

Figure 6A:
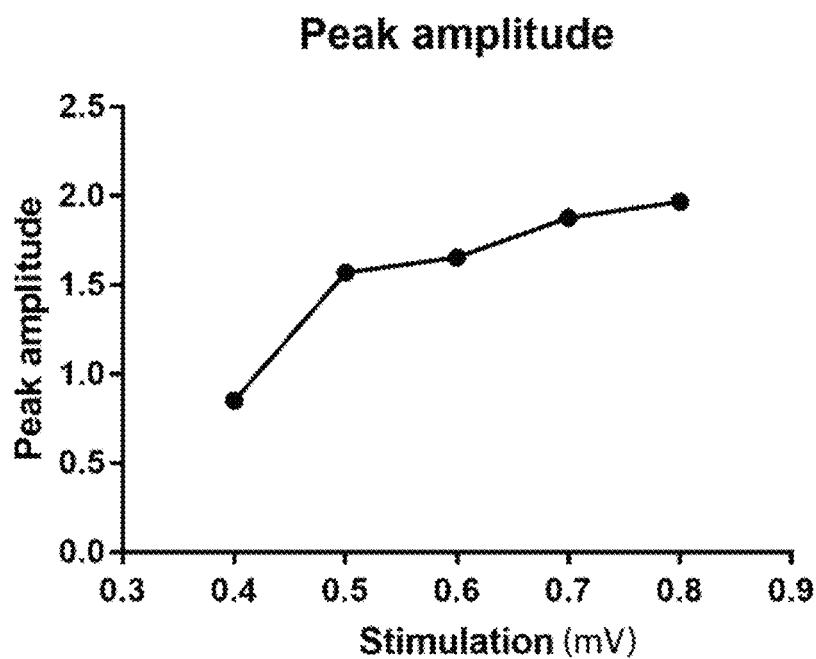
FIG. 6A is a line graph of recording capabilities of a neuromodulation device, as described herein.
Figure 6B:
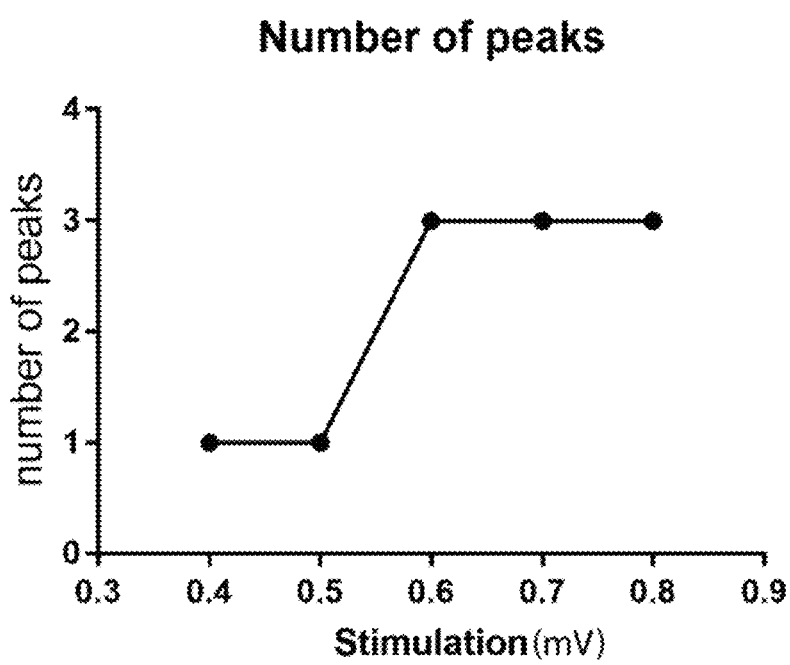
FIG. 6B is a line graph of recording capabilities of a neuromodulation device, as described herein.

FIG. 6 shows recording capabilities of neuroclip. FIG. 6A shows increasing largest peak amplitude of recorded CENG with increasing stimulation amplitude. FIG. 6B shows increasing number of peaks with increasing stimulation amplitude indicated activation of more fibers. Increased amplitude of the stimulation post threshold gave rise to an increase of peak-to-peak amplitude of first peak in compound action potentials indicating increased activation of motor fibers for muscle recruitment. Further increasing the amplitude to 0.9 mV gave rise to secondary peaks corresponding to recruitment of slower fiber types.

Figures 7A, 7B:
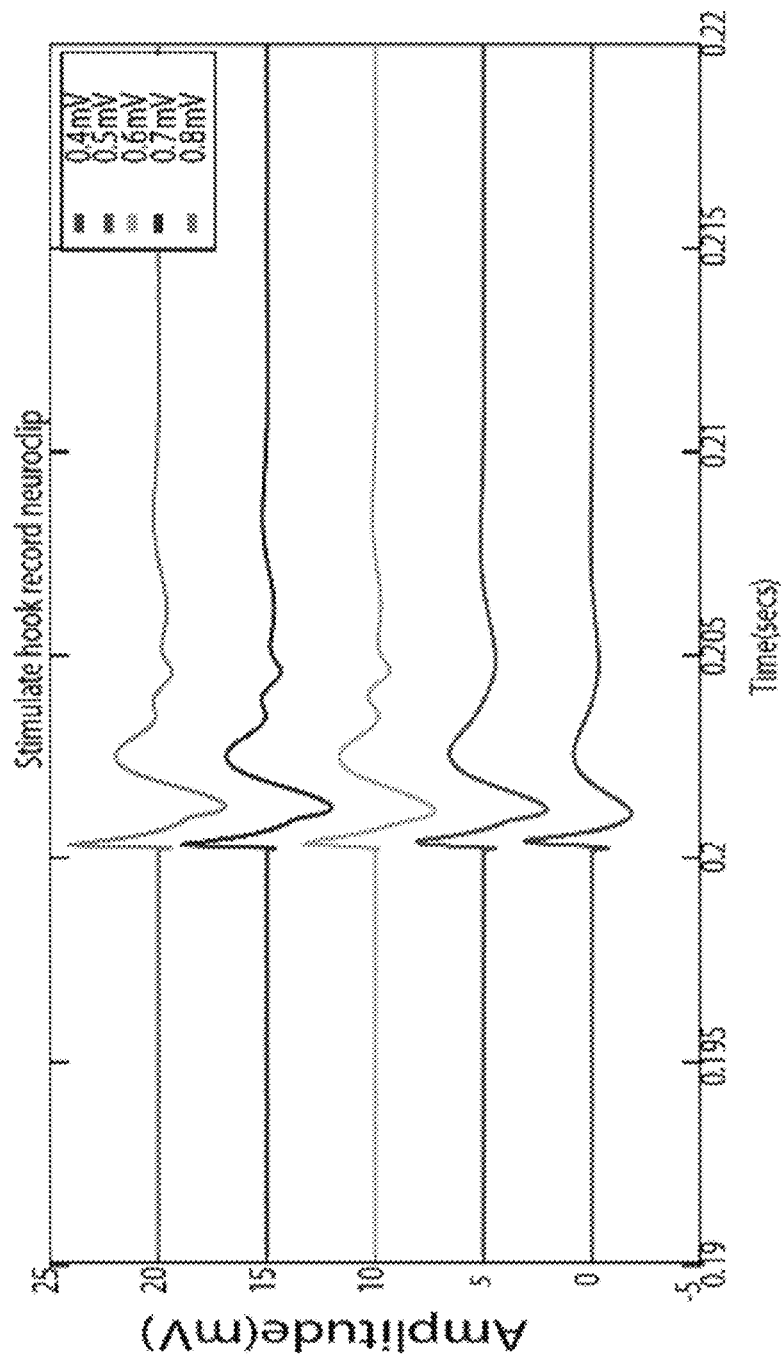
FIG. 7A is a schematic of a stimulating hook electrode and recording neuromodulation device.
FIG. 7B is a line graph of recording capabilities of a neuromodulation device, as described herein, using a hook electrode.

Increasing stimulus amplitude post threshold gives rise to increasing limb recruitment observation in recorded EMGs. FIG. 7 illustrates testing of recording capabilities of neuroclip based on electrical stimulation by a hook electrode [n=3]. Neurograms of compound action potentials were recorded with the implanted neuroclip in response to proximal hook stimulation on DPN. The distance between the two electrodes was about 2±0.5 mm. The stimulation parameters were same as reported above with randomized testing blocks for each trial. Stimulation using a hook electrode showed increased activation of fibers with increased stimulation amplitude. Increased activity is captured in compound action potentials post threshold hook stimulation. The stimulation threshold for recorded compound action potentials by the neuroclip was 0.5±0.1 mV for a visible muscle twitch.

Figure 8A:
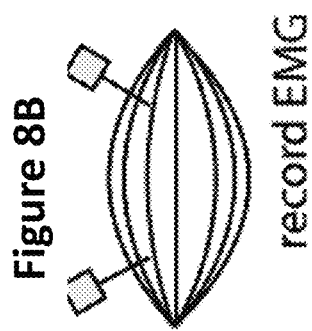
FIG. 8A is a schematic of a neuromodulation device with a stimulating electrode.
Figure 8B:
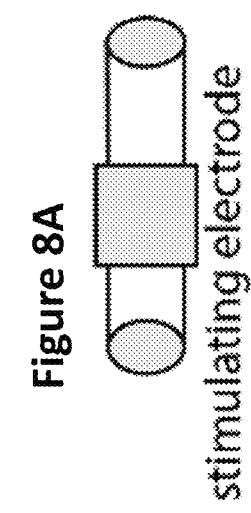
FIG. 8B is a schematic of a recording device that is not within the scope of neuromodulation devices described herein.
Figure 8C:
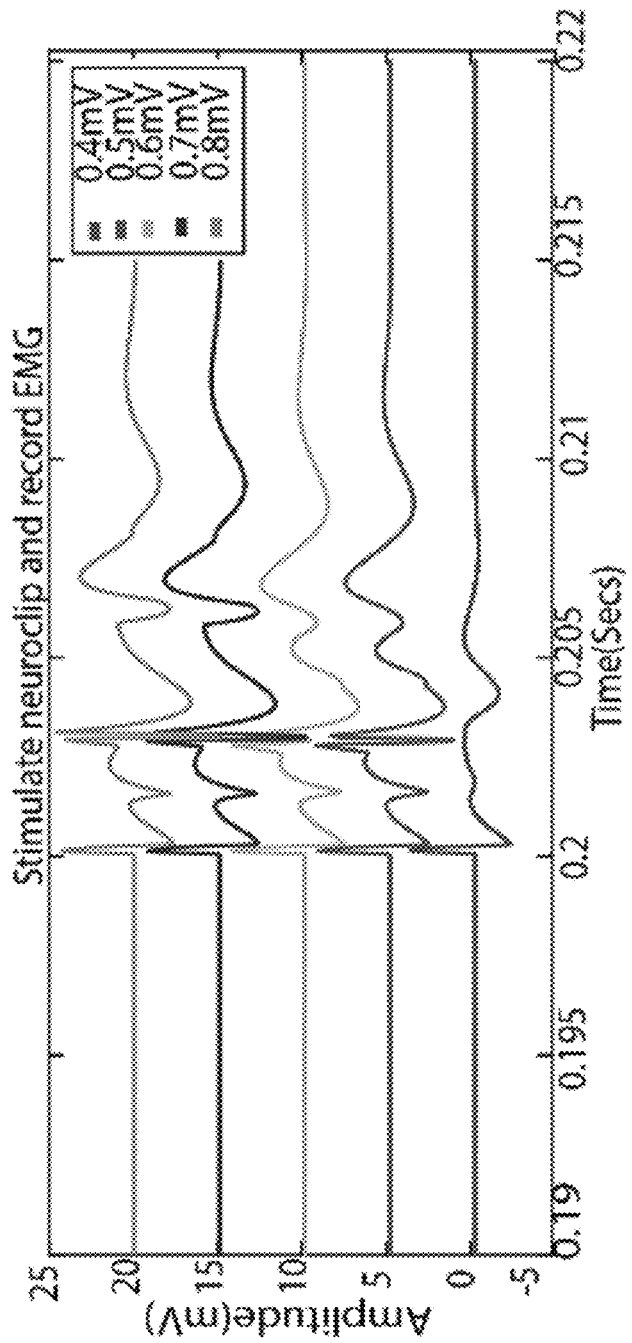
FIG. 8C is a line graph of stimulation capabilities of a neuromodulation device, as described herein.
Figure 9:
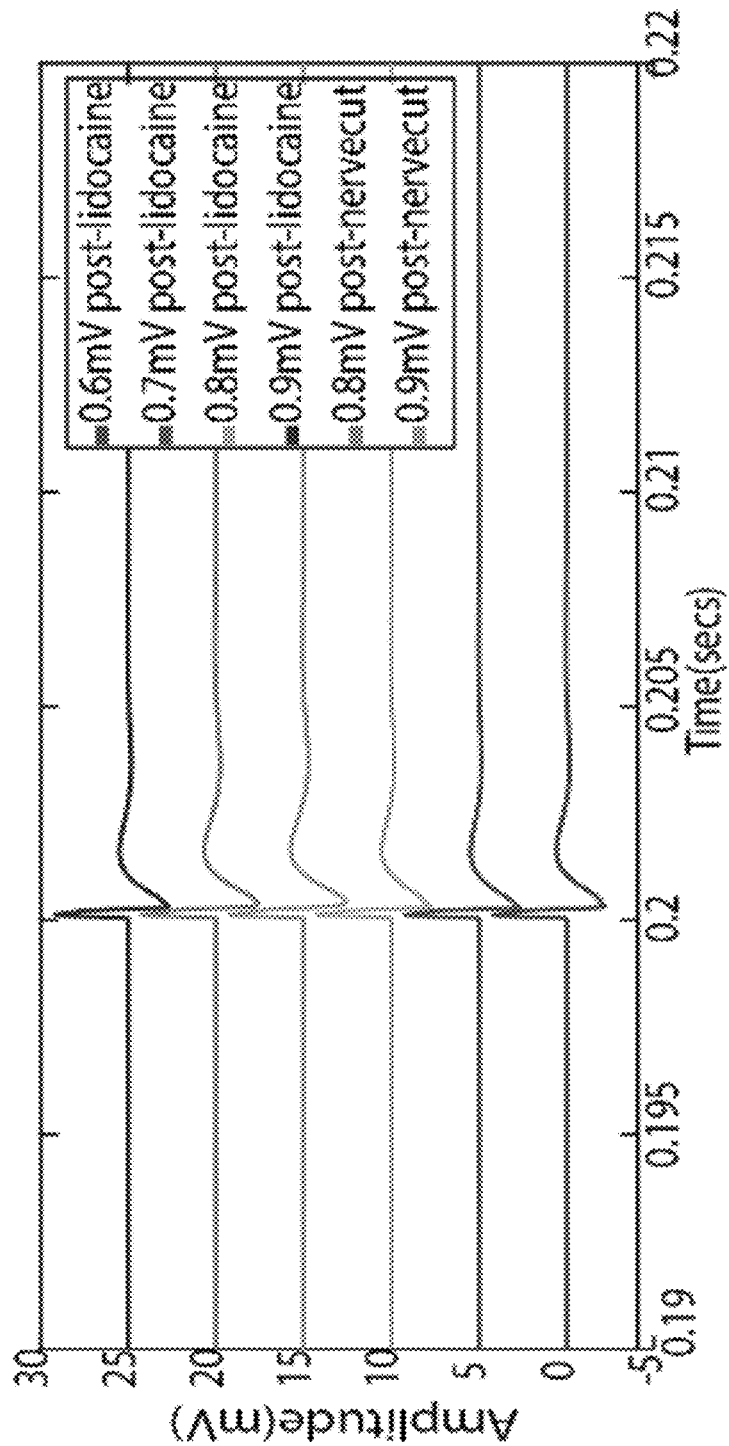
FIG. 9 is a line graph of a control experiment to test the stimulation capabilities of a neuromodulation device, as described herein.

FIG. 8 illustrates the stimulation capabilities of the neuroclip. EMGs recorded from the TA muscle while stimulating using neuroclip show increased response with increased stimulation amplitude. FIG. 9 shows control experiments wherein EMGs were recorded post lidocaine and nerve cut, which show only a stimulation artifact, indicating that the response previously recorded was due to neural stimulation.

A number of small peripheral neural interfaces including nerve cuffs and wired or wireless systems can be used to neuromodulate these small nerves and fascicles.

It should be especially noted that devices 100 described herein, in some embodiments, do not need to be "open" for nerve insertion, nor "closed" after nerve placement. Instead, devices 100 described herein can retain nerves without carrying out such additional steps or modifications of the device 100 structure.

Additionally, described herein are Implantable Neural Interfaces for chronic neuromodulation (recording, stimulation and blocking potential) which provide a) safe and reliable long-term interfacing, b) selectivity, c) low signal to noise ratio, and d) adaptability for varied nerve geometries. This device can be used for the bidirectional link with robotic prosthetic devices, peripheral neuromodulation and bioelectronic medicine applications.

Example 5

Neuromodulation of Pelvic Floor Muscles

To illustrate various features of the disclosure, an exemplary wireless device was implanted into several motor branches innervating individual pelvic floor muscles in healthy young and old adult female rabbits. The results are presented below in the context of FIGS. 11-14.

Figure 11:
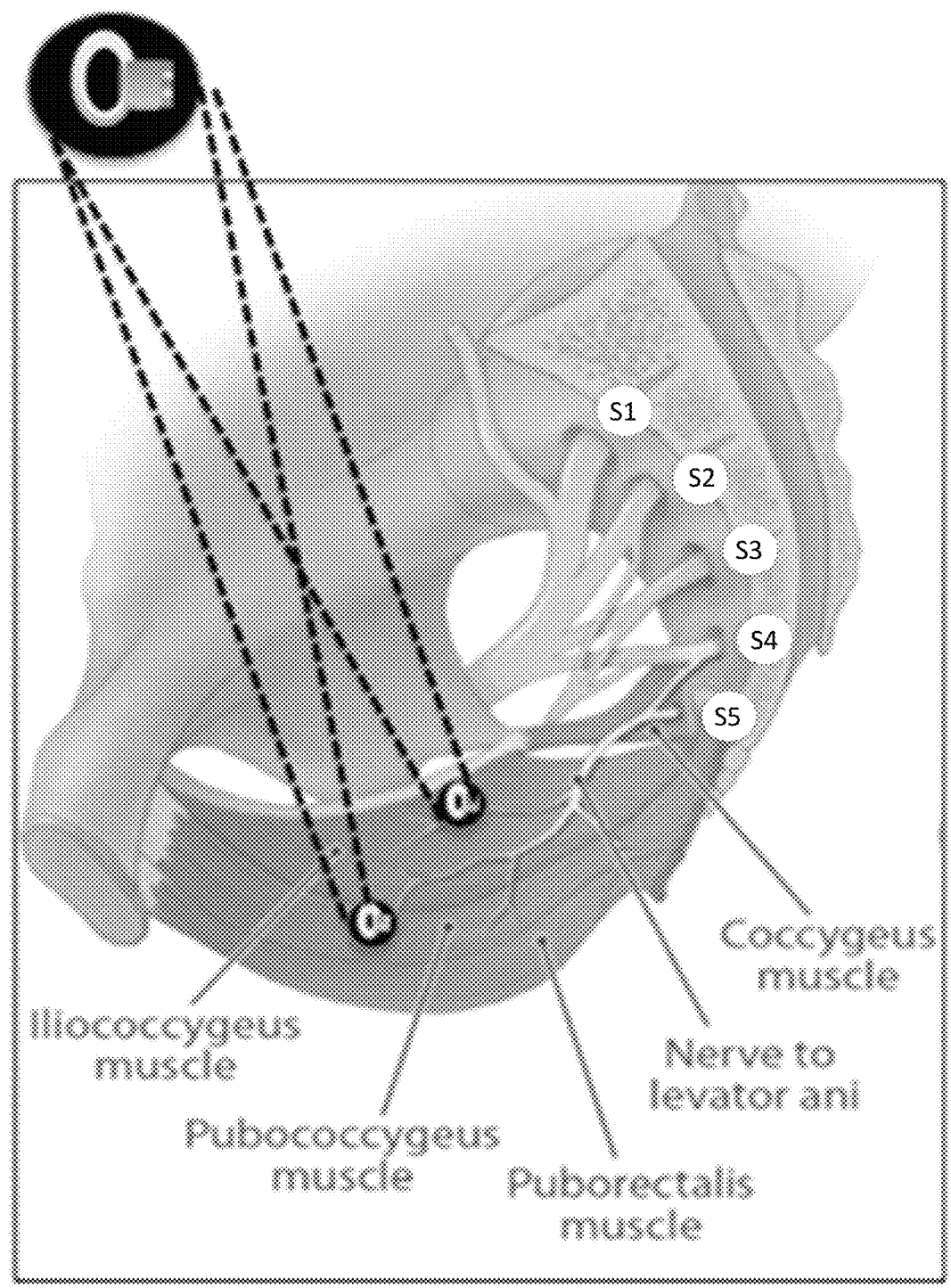
FIG. 11 is a cartoon representation of methods of neuromodulation, as described herein.

FIG. 11 illustrates an example nerve cuff placed onto the small nerves controlling the pelvic muscles.

Figure 12A:
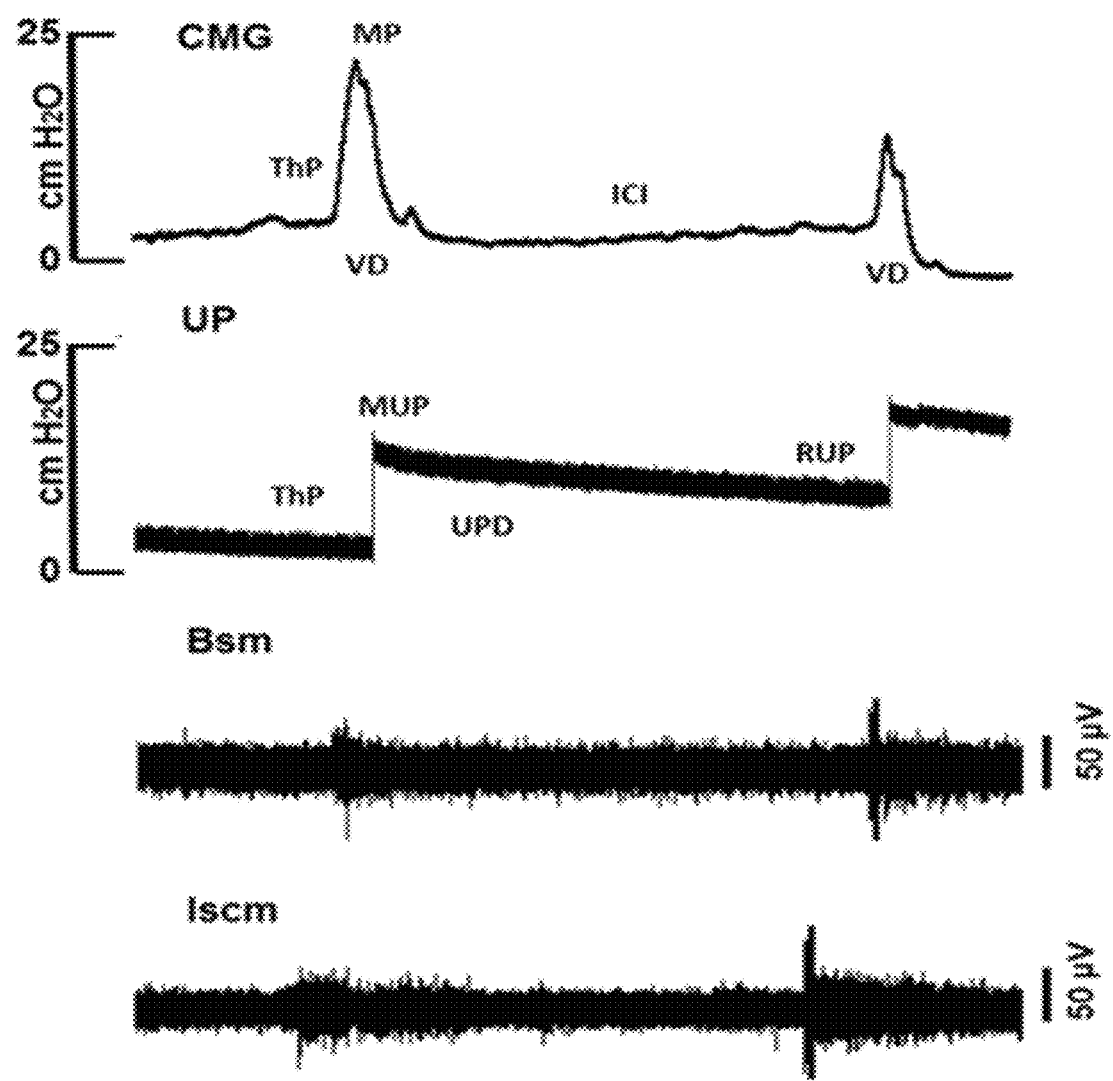
FIG. 12A is electromyogram recordings of rabbit pelvic floor muscles.
Figure 12B:
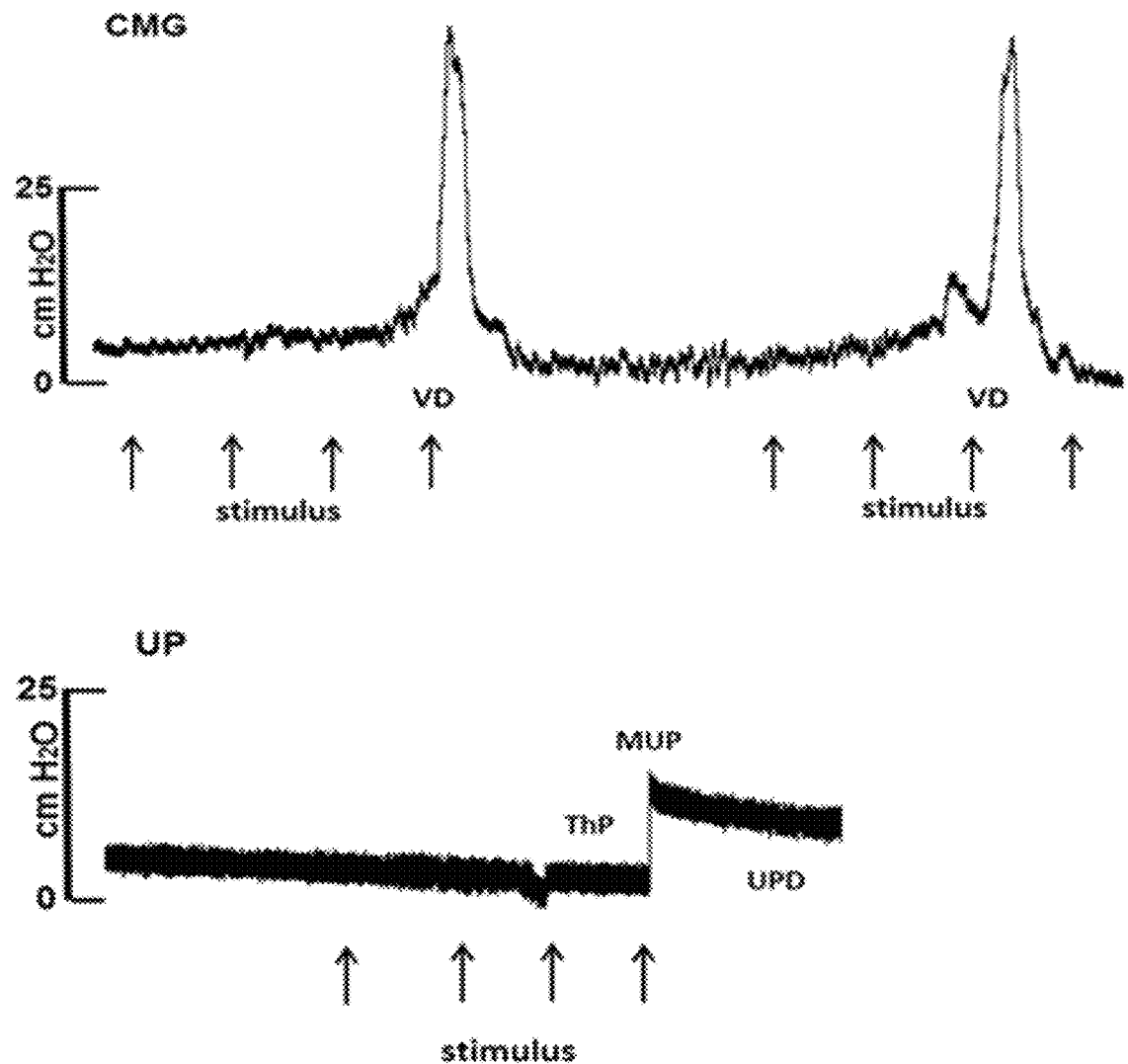
FIG. 12B is electromyogram recordings of rabbit pelvic floor muscles.

FIG. 12 shows the normal urodynamic response of a young nulliparous rabbit (FIG. 12A) and how the bladder storage capacity and voiding efficiency in response to direct Bsm acutely in anesthetized animals. Stimulation of this nerve at 2 Hz for 10 min induced voiding and improving storage capacity by neuromodulation of nerves controlling individual pelvic floor muscles.

Figure 13A:
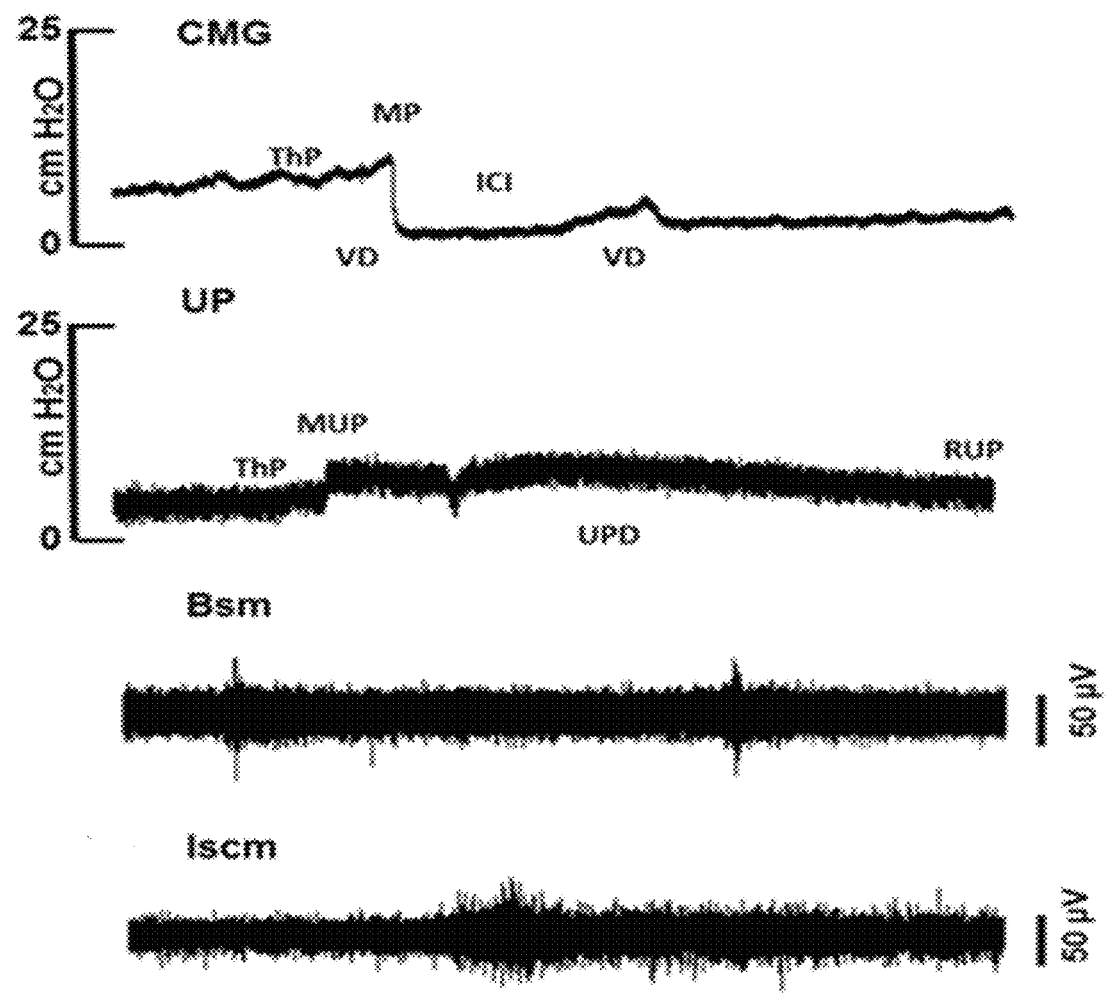
FIG. 13A is electromyogram recordings of rabbit pelvic floor muscles.
Figure 13B:
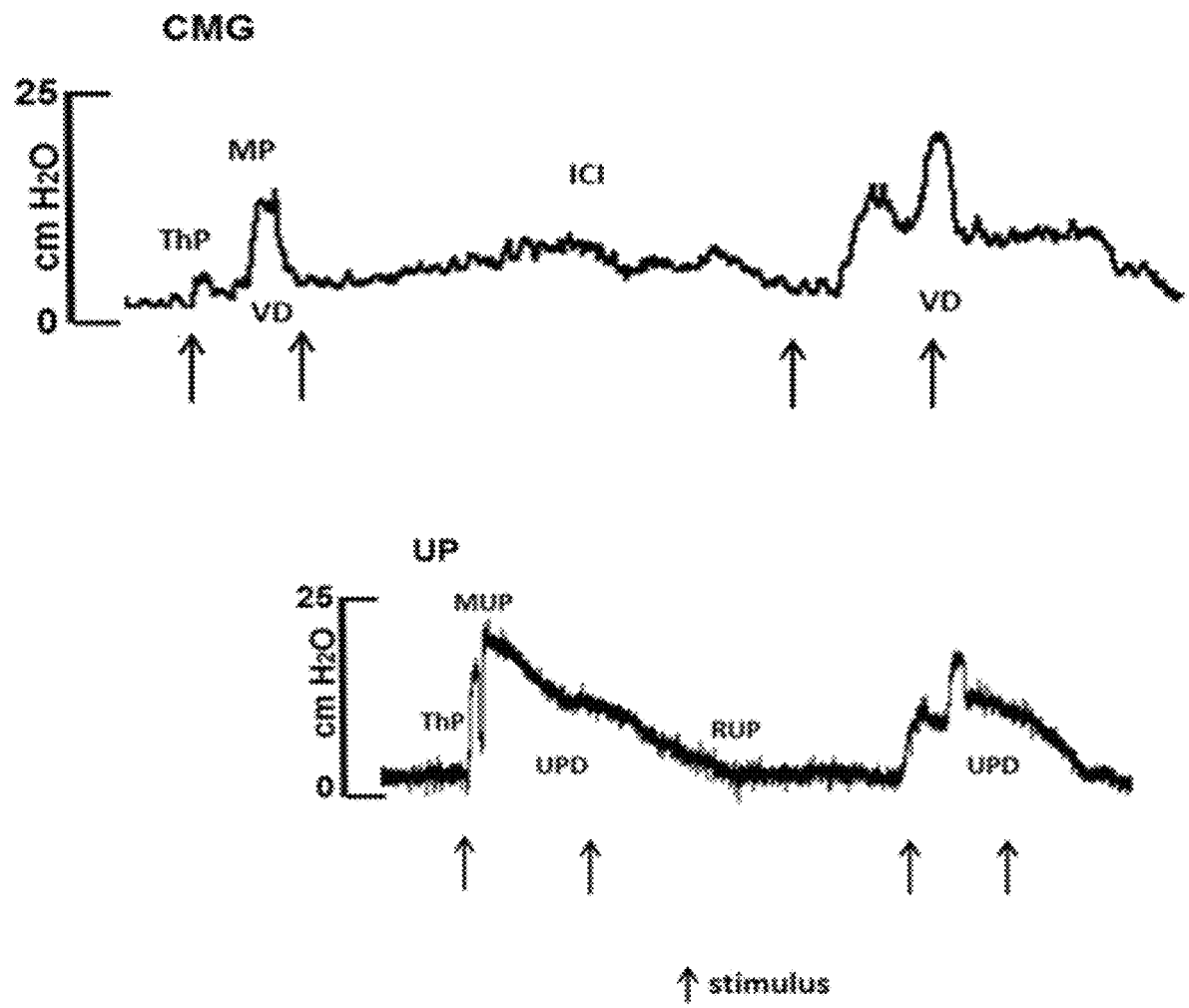
FIG. 13B is electromyogram recordings of rabbit pelvic floor muscles.

FIG. 13A illustrates how the severely compromised bladder function in 3-4 year old rabbits, showing less than 12.5 cm H2O with a corresponding reduction of urethral pressure to approximately 20-30% of that in a normal animal. Not intending to be bound by theory, it is believed that the deficit in the reported animal may be the result of Bsm and Icm muscle dyssynergia. After specific neuromodulation of the pelvic floor muscles these animals showed immediate improvements in symptoms and visible improvement in urine stream, resembling that characteristic of younger animals. After electrical stimulation of the Bsm nerve we observed a significant increase in both urine volume and urethral pressure.

In old nulliparous rabbits the synergy between the bladder and urethral function are expected to be dysfunctional due to neurogenic, myogenic or mixed factors, resulting in inefficient activity of Bsm and Iscm. If the nerve and muscle are at least partially functional, PFNS may reverse the effects on bladder and urethral dysfunction characteristics, through increased voiding efficiency, the maximum urethral pressure and urethral closure.

Figure 14A:
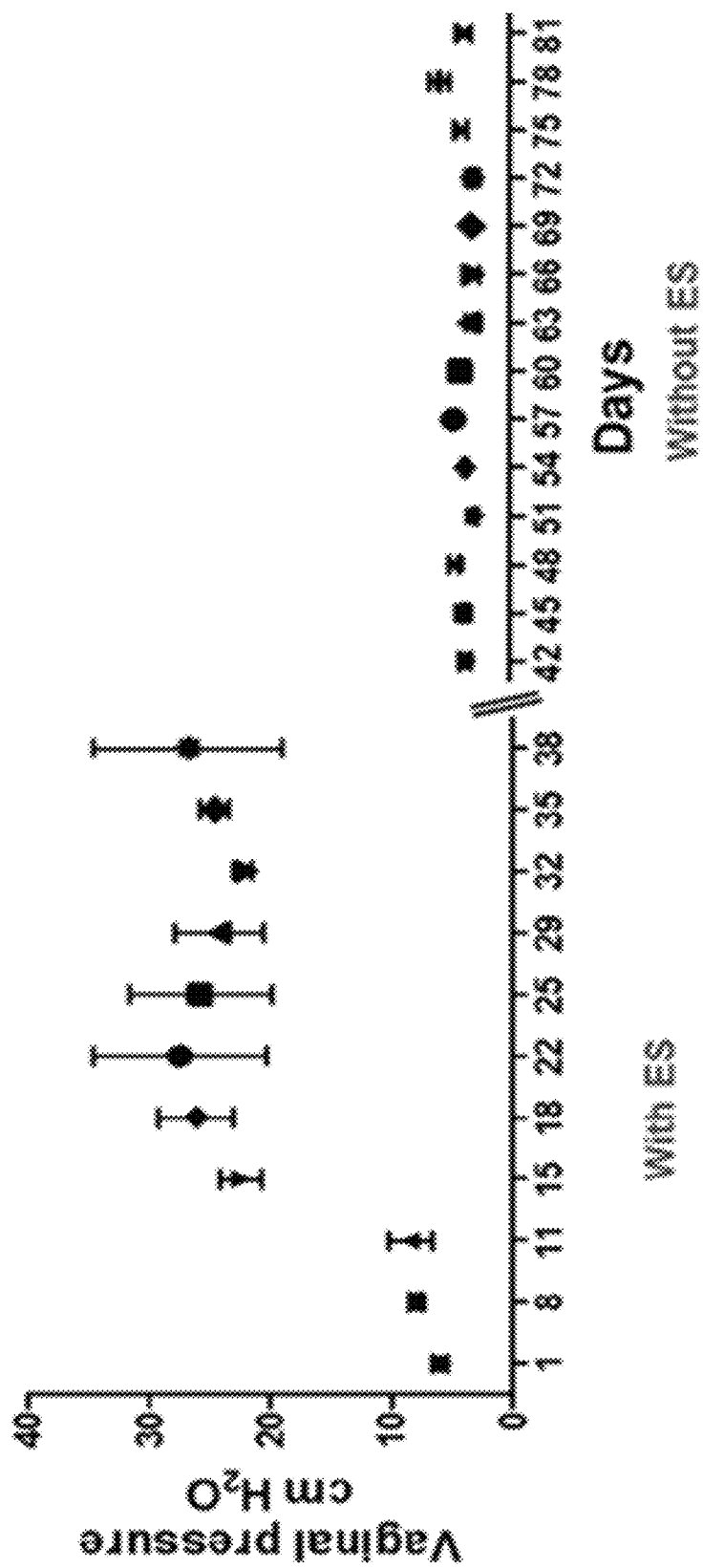
FIG. 14A is a graph of vaginal pressure in rabbits.
Figure 14B:
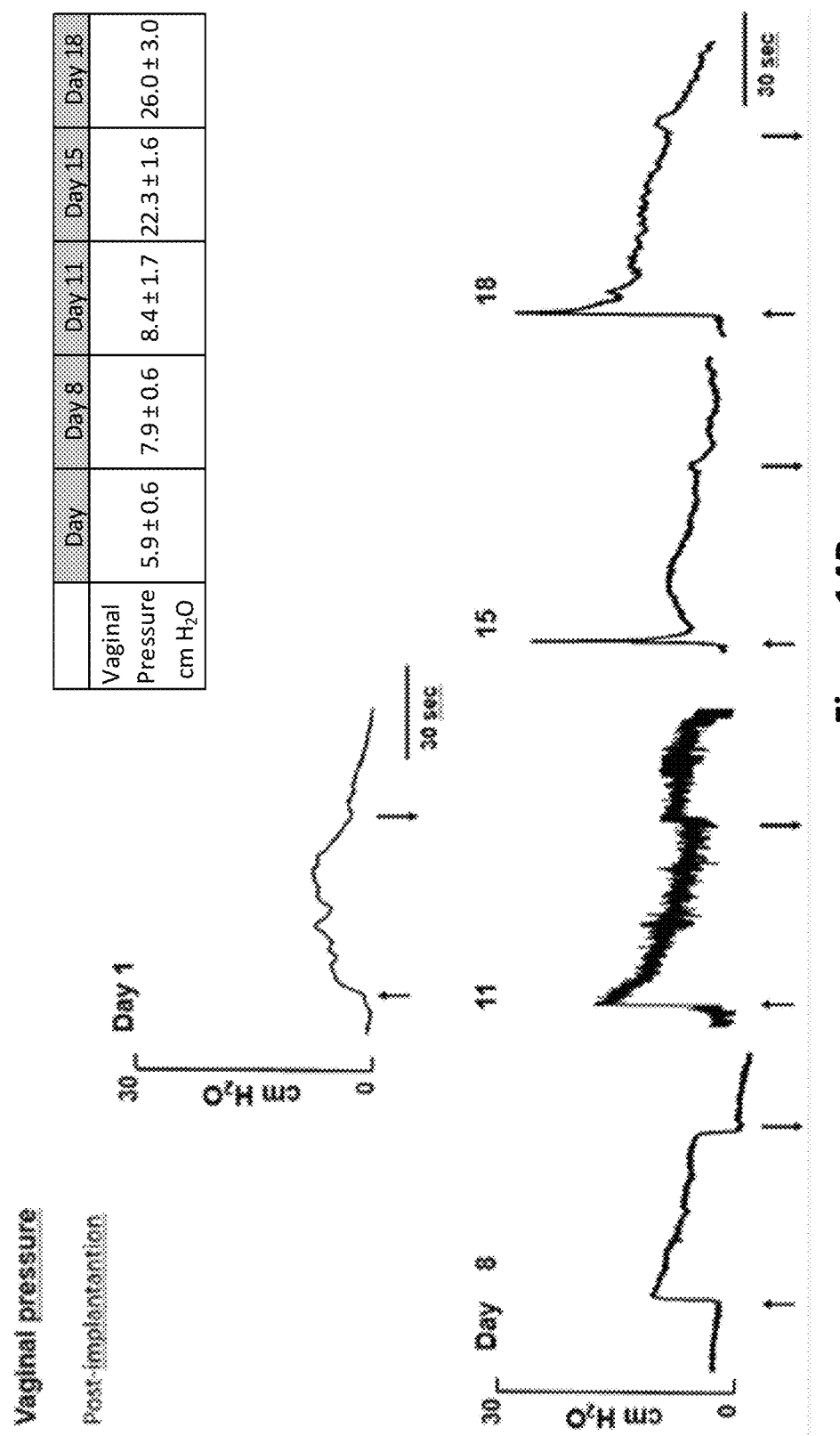
FIG. 14B is a graph of vaginal pressure in rabbits.

FIG. 14 shows the implanted and stimulated onto the Icm on a young animal who received 10 min of stimulation at 2 Hz and 40% amplitude levels 3 times per week while fully awake for 38 days. An intravaginal pressure sensor was used to determine the effect of the treatment at several time points as contraction of the Icm increases vaginal pressure.

An "ON-OFF" protocol was followed with 38 days for stimulation and discontinued thereafter. We were able to show a slight effect on the first week, which increased 15 days after implantation, reaching an overall 3-fold strengthening of the PFM plateauing thereafter.

Discontinuation of the electric stimulation of this nerve for 43 days regressed the activity to base-line levels. This result provides robust evidence of the benefit of specific pelvic floor nerve modulation.

Example 6

Wireless Stimulation of Pelvic Floor Motor Efferents Neuromodulate Micturition in Female Rabbits More than 40% of women suffer from lower urinary tract (LUT) disorders including deficient bladder emptying and urinary incontinence. Electrical stimulation of the S3-S4 root or the pudendal plexus that innervate several pelvic and perineal targets is considered currently a viable alternative treatment of several LUT dysfunctions. However, this therapy seems to increase urinary retention in some patients, and urinary voiding in others. These contradictory effects seem to be, at least in part, due to the indiscriminatory activation of both efferent and afferent fibers in the sacral or pudendal plexi in the pelvic floor. We sought to investigate whether stimulation of the specific motor efferent innervating the ischiocavernosus, (Icm) and bulbospongiosus (Bsm) muscles in the pelvic floor would modulate the bladder emptying response. We believe these muscles deploy asynchronous activity during urine storage and bladder emptying. Nulliparous adult young female rabbits were implanted acutely with a novel wireless miniature cuff electrode (WMCE) that uses RF at a 10.7 MHz frequency to power a 1 mm transistor-less device attached to a custom nerve cuff. A diode in the WMCE was used to produce a 400 us cathodic pulse and deliver a 400 mV potential to the target nerves. The animals were stimulated for 30 seconds at 2 Hz and repeated 3 times with a 10-minute inter-stimulation delay. Cystometrograms were recorded before and during the WMCE stimulation and the threshold volume of the bladder, voided and residual volume, and the voiding efficiency were quantified. The results showed that wireless stimulation of the Bsm and Ism nerves the increase the maximum pressure of the bladder. These results demonstrate the efficacy of wireless neuromodulation of perineal muscle nerves for affecting bladder function. We describe herein an approach (including systems, devices, and methods) that can, in some cases, offer a more selective treatment for urinary incontinence.

Example 7

Selective Stimulation of Pelvic Floor Muscles

Impaired bladder emptying is a common clinical condition exhibiting lower urinary tract symptoms (LUTS) that affect almost 25% of the female and 10% of male population in the US alone. The underactive bladder (UAB) and detrusor underactivity (DU) are common types of LUTS. Summated the implications of menopause with to aging, most women spend more than a third of life with pelvic floor dysfunctions apparently exacerbated during aging. The PMF muscles, namely the bulbospongiosus and bulbocoxigeous nerves, innervate muscles of the same name. These pelvic muscles are part of a complex neuro-muscular coordination of the lower urinary tract (LUT) and play a critical role in the control of micturition, defecation and sexual functions. Moreover, damage to the LUT due to childbirth, trauma, or aging results in urinary incontinence.

Figure 10:
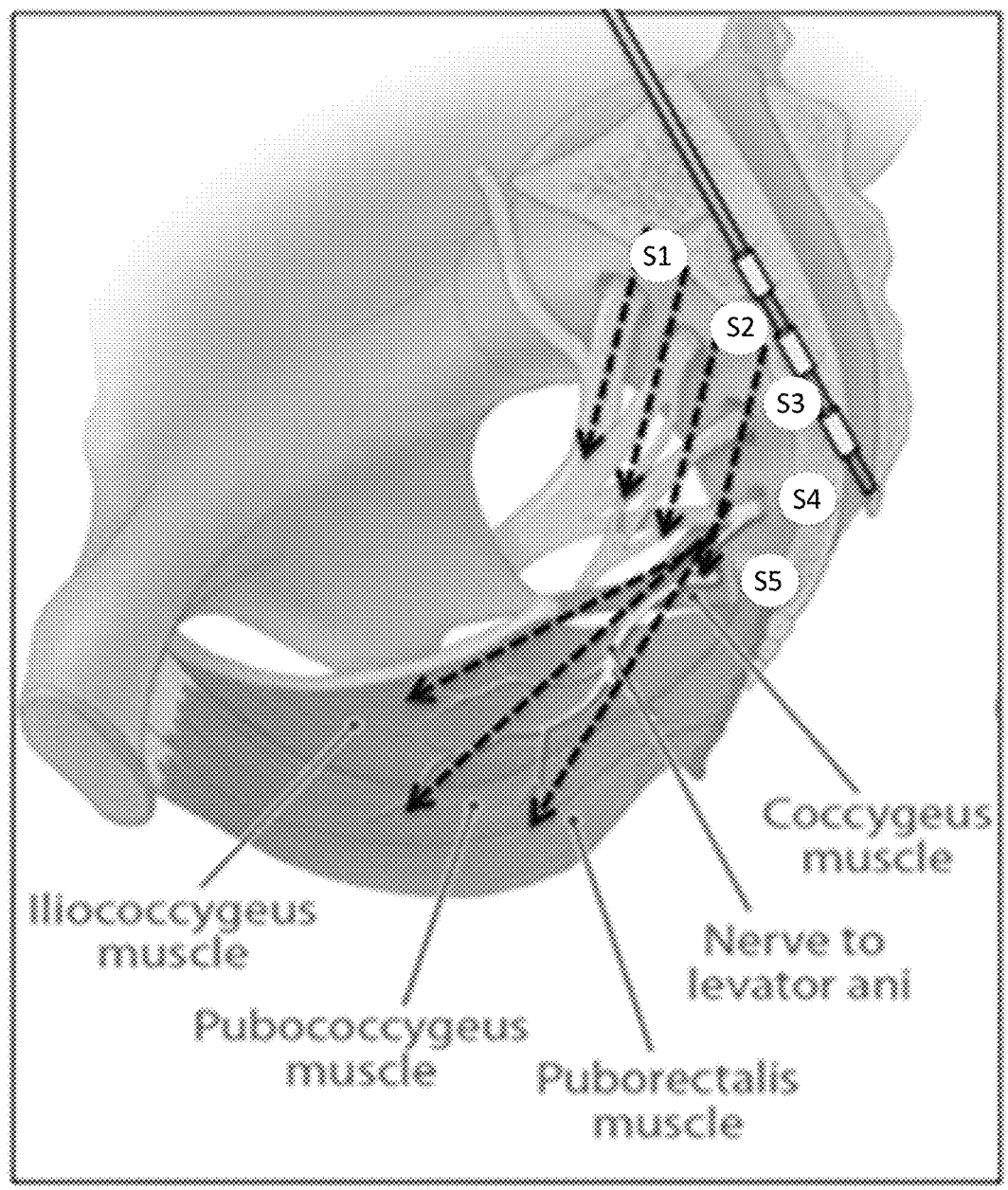
FIG. 10 is a cartoon representation of Prior Art methods of neuromodulation.

Electrical stimulation of the sacral nerves (S3-S4) innervate pelvic and perineal targets, and has been an established method for the management of several urinary tract dysfunctions since 1997, particularly of overactive bladder (OAB) (FIG. 10). Medtronic's Interstim™ device has been implanted in more than 200,000 patients globally, and the efficacy has been reported to be 50% in mediating urinary retention. It is believed that stimulation of afferent sensory fibers negatively modulates excitatory synapses in the central micturition reflex pathway.

However, neuromodulation has not been widely accepted as a first-line treatment for urinary incontinence, and its use is reserved for those unresponsive to all other treatments. At least in part, this is due to the fact that therapeutic mechanism are not understood, particularly when the therapy seems to mediate increase urinary retention in some patients and urinary voiding in others. There is also much disagreement as to whether the pelvic afferents or efferents nerves are needed, and whether direct or polysynaptic reflex mediate the effect. The contradictory results may be explained at least in part by the non-specific nature of the treatment as S3-S4 nerves branch into the hypogastric nerve (afferent sensory/efferent sympathetic), and the pelvic nerve (afferent sensory, efferent somatic), which provides innervation to the urethra, the external anal sphincter, the levator ani muscles, the perineal skin, and the clitoris. Furthermore, there are significant variations with respect to the origin and course of the pudendal, levator ani, and inferior rectal nerves that make the application of the therapy uncertain and difficult to standardize.

We disclose herein that neuromodulation of the bulbospongiosus nerve can re-establish a normal micruition pattern in a rabbit model of urinary incontinence. We further describe the clinical benefit of direct and specific control of small PFM.

Applications of the present disclosure include the access of small nerves which are traditionally difficult due to size and location, such as the clitoris nerve.

Group unilateral electrical stimulation of Bsm nerve in young nulliparous rabbits: Before of electrical stimulation of the Bsm nerve the recordings of cystometrogram (FIG. 13A), urethral pressure (FIG. 13A) and electromyogram activity from perineal muscles (FIG. 13A) were simultaneously obtained in YN. Both storage and voiding phases of micturition were observed (FIG. 13A).

Group unilateral electrical stimulation of Bsm nerve in old multiparous rabbits:

FIG. 1: Electromyogram recordings of (FIG. 13A, Bsm) and (FIG. 13A, Ism) muscles during the micturition and with electrical stimulation of Bsm nerve (FIG. 13B) in anesthetized old multiparous rabbits.

Storage and voiding phases of the micturition are indicated. ThP; MP; VD; ICI; ThP, threshold urethral pressure; MUP; UPD; RUP, pressure to return to baseline; s, seconds. Electrical stimulation of Bsm nerve. Before of electrical stimulation of Bsm nerve was observed that the multiparity and age affected bladder (A), urethral function (B) and activity pattern of perineal muscle (C, D). Detrusor muscle contraction decreased. Electrical stimulation proved to total bladder volume and the urethral pressure, significantly improving the urinary incontinence condition in the rabbit.

We have also shown the chronic neuromodulation of the Isch motor nerve. See FIG. 14: Vaginal pressure during the electrostimulation of Iscm nerve postimplantation of miniature wireless nerve cuff electrode in young nulliparous rabbit. The stimulation of Iscm nerve produced different changes of vaginal pressure in the first day postimplantation of miniature wireless nerve cuff electrode elevated the pressure of the vagina at 1, 8, 11, 15 and 18 days. ↑ starting stimulation, ↓ finishing stimulation. Novel and discriminatory factors described herein include the selectivity of the stimulation by targeting small nerve branches that directly innervate specific organs.

The invention claimed is:

1. An implantable neuromodulation device comprising:
a chamber configured to receive a nerve, the chamber having a cross-sectional chamber inner dimension;
at least one electrode disposed in the chamber; and
a channel having a cross-sectional channel dimension that is smaller than a cross-sectional chamber dimension, the channel having a proximal end and a distal end, proximal end being open to outside of the device and the distal end terminating at the chamber, the channel fluidly connecting an interior of the chamber with an exterior of the neuromodulation device such that the chamber is fluidly connected to the exterior of the neuromodulation device, the cross-sectional channel inner dimension being fixed, the channel having a central line that changes direction from the proximal end to the distal end,
the channel being defined by at least a first wall portion, a second wall portion, a third wall portion, and a fourth wall portion, the first and second wall portions being at or proximate to the proximal end, the third and fourth wall portions being at or proximate to the distal end, each of the third and fourth wall portions being oriented transversely to each of the first and second wall portions,
the central line having a first segment passing between the first and second wall portions and a second segment passing between the third and fourth wall portions, such that the first and second segments are oriented transversely to each other, and such that passing a nerve through the non-linear channel from the proximal end to the chamber requires changing direction, wherein the cross-sectional channel inner dimension is smaller than the maximum diameter of the nerve.

2. The implantable neuromodulation device of claim 1, wherein the channel has a constant diameter.

3. An implantable neuromodulation device comprising:
a chamber configured to receive a nerve, the chamber having a cross-sectional chamber inner dimension;
at least one electrode disposed in the chamber; and
a non-linear channel having a proximal end and a distal end, the proximal end being open to outside of the device and the distal end terminating at the chamber, the non-linear channel fluidly connecting an interior of the chamber with an exterior of the neuromodulation device such that the chamber is fluidly connected to the exterior of the neuromodulation device, the non-linear channel having a cross-sectional channel inner dimension at the distal end, and wherein the cross-sectional channel inner dimension at the distal end is less than the cross-sectional chamber inner dimension, wherein the channel is configured to remain continuously open, the channel having a central line that changes direction from the proximal end to the distal end,
the non-linear channel being defined by at least a first wall portion, a second wall portion, a third wall portion, and a fourth wall portion, the first and second wall portions being at or proximate to the proximal end, the third wall portion being adjacent the first wall portion, and fourth wall portion being adjacent to the second wall portion, each of the third and fourth wall portions being oriented transversely to each of the first and second wall portions,
the central line having a first segment passing between the first and second wall portions and a second segment passing between the third and fourth wall portions, such that the first and second segments are oriented transversely to each other, and such that passing a nerve through the non-linear channel from the proximal end to the chamber requires changing direction,
wherein the cross-sectional channel inner dimension is smaller than the maximum diameter of the nerve.

4. The implantable neuromodulation device of claim 3, wherein the channel is configured to remain continuously open after a nerve is positioned in the chamber.

5. The implantable neuromodulation device of claim 3, wherein the channel is configured to remain continuously open when a nerve is stimulated in the chamber.

6. An implantable neuromodulation device comprising:
a chamber configured to receive a nerve, the chamber having a cross-sectional chamber inner dimension;
at least one electrode disposed in the chamber; and
a non-linear channel having a proximal end and a distal end, the proximal end being open to outside of the device and the distal end terminating at the chamber,
the non-linear channel being defined by at least a first wall portion, a second wall portion, a third wall portion, and a fourth wall portion, the first and second wall portions being at or proximate to the proximal end, the third and fourth wall portions being at or proximate to the distal end, each of the third and fourth wall portions being oriented transversely to each of the first and second wall portions, the non-linear channel fluidly connecting an interior of the chamber with an exterior of the neuromodulation device such that the chamber is fluidly connected to the exterior of the neuromodulation device, the non-linear channel having a cross-sectional channel inner dimension at the distal end, and wherein the cross-sectional channel inner dimension at the distal end is less than the cross-sectional chamber inner dimension, the cross-sectional channel inner dimension at the distal end being fixed, the non-linear channel having a central line that extends from the proximal end to the distal end, the central line having a first segment passing between the first and second wall portions and a second segment passing between the third and fourth wall portions, the central line changing direction from the proximal end to the distal end, such that the first and second segments are oriented transversely to each other, and such that passing a nerve through the non-linear channel from the proximal end to the chamber requires changing direction, wherein the cross-sectional channel inner dimension is smaller than the maximum diameter of the nerve.

7. The implantable neuromodulation device of claim 6, wherein the channel comprises a diameter between 50 to 5000 micrometers.

8. The implantable neuromodulation device of claim 6, wherein the at least one electrode is configured to at least one of record or apply electrical impulses.

9. The implantable neuromodulation device of claim 6, wherein the non-linear channel is L-shaped.

10. The implantable neuromodulation device of claim 6, wherein the non-linear channel has a diameter that is 10% to 40% smaller than a diameter of the nerve.

11. The implantable neuromodulation device of claim 6, wherein the at least one electrode comprises at least one of gold, platinum, iridium oxide, carbon nanotubes, graphene, titanium nitride, and iridium.

12. The implantable neuromodulation device of claim 6, further comprising:
a stimulation generator configured to provide an electrical pulse to the at least one electrode.

13. The implantable neuromodulation device of claim 12, wherein the at least one electrode is configured to apply an electrical stimulation having an amplitude between 9.5 microAmps to 20 milliAmps, wherein the electrical stimulation is received from the stimulation generator.

14. The implantable neuromodulation device of claim 12, wherein the at least one electrode is configured to apply an electrical stimulation having a voltage of between 0.1-10 V, wherein the electrical stimulation is received from the stimulation generator.

15. The implantable neuromodulation device of claim 12, wherein the at least one electrode is configured to apply an electrical stimulation at a frequency between 0.5 to 50 KHz, wherein the electrical stimulation is received from the stimulation generator.

16. The implantable neuromodulation device of claim 6, wherein the at least one electrode is configured to apply an electrical stimulation having at least one of a square, monopolar, cathodic, or bipolar balanced shape, wherein the electrical stimulation is received from a stimulation generator.

17. The implantable neuromodulation device of claim 6, wherein the at least one electrode is configured to apply an electrical stimulation having a pulse with a duration between 20-500 microseconds, wherein the electrical stimulation is received from a stimulation generator.

18. The implantable neuromodulation device of claim 6, wherein the at least one electrode is disposed on at least one wall of the chamber.

19. The implantable neuromodulation device of claim 6, wherein the channel is configured to compress a nerve.

* * * * *